United States Patent
Chen et al.

(10) Patent No.: US 12,068,071 B2
(45) Date of Patent: Aug. 20, 2024

(54) SYSTEM AND METHOD OF DYNAMICALLY GENERATING WORK ASSIGNMENTS

(71) Applicant: CVS Pharmacy, Inc., Woonsocket, RI (US)

(72) Inventors: Caroline L. Chen, Natick, MA (US); Jared P. Tancrelle, Smithfield, RI (US)

(73) Assignee: CVS Pharmacy, Inc., Woonsocket, RI (US)

( * ) Notice: Subject to any disclaimer, the term of this patent is extended or adjusted under 35 U.S.C. 154(b) by 0 days.

(21) Appl. No.: 18/163,189

(22) Filed: Feb. 1, 2023

(65) Prior Publication Data

US 2023/0178228 A1 Jun. 8, 2023

Related U.S. Application Data

(63) Continuation of application No. 16/855,531, filed on Apr. 22, 2020, now Pat. No. 11,610,670.
(Continued)

(51) Int. Cl.
*G16H 40/20* (2018.01)
*G06N 5/02* (2023.01)
(Continued)

(52) U.S. Cl.
CPC .............. *G16H 40/20* (2018.01); *G06N 5/027* (2013.01); *G06Q 10/06312* (2013.01);
(Continued)

(58) Field of Classification Search
CPC ..................................................... G16H 40/20
See application file for complete search history.

(56) References Cited

U.S. PATENT DOCUMENTS

| 7,827,041 B2 | 11/2010 | Roberts et al. |
| 8,554,581 B2 | 10/2013 | Roberts et al. |

(Continued)

FOREIGN PATENT DOCUMENTS

| WO | 20210050926 | 5/2010 | |
| WO | WO-2010050926 A1 * | 5/2010 | ............. G06Q 10/06 |

OTHER PUBLICATIONS

NDIA, Planning & Scheduling Excellence Guide (PASEG), Version 3.0, Mar. 9, 2016. (Year: 2016).*
(Continued)

*Primary Examiner* — Kurtis Gills
(74) *Attorney, Agent, or Firm* — Patent Law Works LLP

(57) ABSTRACT

Example systems and methods provide dynamic generation and display of workstation assignments in a pharmacy information system. A plurality of electronic workstation displays are in network communication with a workstation assignment engine configured to generate workstation assignments for employees assigned to the workstations displays and store a schedule record. Based on various triggers, workstations identified in the workstation assignments display the workstation assignments on a graphical user interface portion of the workstation displays. Dynamically generated changes to the workstation assignments in the schedule record may be generated and displayed in response to real-time change in coverage events.

20 Claims, 12 Drawing Sheets

Related U.S. Application Data

(60) Provisional application No. 62/838,762, filed on Apr. 25, 2019.

(51) Int. Cl.

| | |
|---|---|
| *G06Q 10/0631* | (2023.01) |
| *G06Q 10/10* | (2023.01) |
| *G06Q 10/1091* | (2023.01) |
| *G06Q 30/018* | (2023.01) |

(52) U.S. Cl.
CPC ..... *G06Q 10/06316* (2013.01); *G06Q 10/103* (2013.01); *G06Q 10/1091* (2013.01); *G06Q 30/018* (2013.01)

(56) References Cited

U.S. PATENT DOCUMENTS

| | | | |
|---|---|---|---|
| 8,688,473 B2 | 4/2014 | Roberts et al. | |
| 2004/0019542 A1* | 1/2004 | Fuchs | G07C 1/14 |
| | | | 705/32 |
| 2005/0149372 A1* | 7/2005 | Kite | G06Q 10/06315 |
| | | | 705/7.22 |
| 2005/0228766 A1* | 10/2005 | Roberts | G06Q 10/10 |
| 2006/0155633 A1 | 7/2006 | Fellenstein et al. | |
| 2008/0301296 A1* | 12/2008 | York | G06Q 10/06 |
| | | | 709/225 |
| 2010/0287002 A1* | 11/2010 | Barre | G06Q 40/08 |
| | | | 705/2 |
| 2011/0166904 A1* | 7/2011 | Arrowood | G06Q 10/06313 |
| | | | 705/7.23 |
| 2012/0089432 A1 | 4/2012 | Podgurny et al. | |
| 2014/0278466 A1* | 9/2014 | Simmons | G16H 20/10 |
| | | | 705/2 |
| 2015/0154528 A1* | 6/2015 | Kharraz Tavakol | |
| | | | G06Q 10/063114 |
| | | | 705/2 |
| 2019/0188625 A1* | 6/2019 | Podgurny | G06Q 10/06 |

OTHER PUBLICATIONS

Montaser et al., "Automated Site Data Acquisition Technologies for Construction Progress Reporting," CSCE 2014 General Conference, May 28-31, 2014, Halifax, Canada, 10 pgs.

\* cited by examiner

SYSTEM AND METHOD OF DYNAMICALLY GENERATING WORK ASSIGNMENTS

BACKGROUND

Customer service has become a main focus and an important means by which many commercial service providers, such as banks, insurance companies, hospitals and retailers, distinguish themselves and remain competitive in their respective markets. Service providers attempt to gain new customers and to retain existing customers by providing and improving service that meets the needs and expectations of their customers. Pharmacies are not immune to competition and similarly rely upon providing and improving customer service to retain and expand customer bases. Data show that a major reason for a customer to switch from one pharmacy to another for such services as drug prescription fulfillment is due to dissatisfaction with the quality of service that a pharmacy provides. In particular, pharmacy service issues are cited as a major reason for substantial loses in annual revenue from prescription sales.

Pharmacy service issues can result from a number of problems that pharmacies and customers experience that can range from a lack of personnel at pharmacy service counters to a lack of adequate communication between pharmacies and customers concerning any problems that cause prescriptions to be delayed, only partially filled or not filled at all. As a result, pharmacies cannot meet customers' needs and expectations, for instance, with respect to promised prescription pick-up times.

Many pharmacies do not attempt to account for the root causes of service issues. For example, a large percentage of drug prescriptions can develop into problem transactions due to, for instance, insurance rejection, lack of pharmacy inventory or lack of authorization for prescription refill. Problems transactions can require separate processes for resolution outside of prescription fulfillment processes. As a result, problem transactions have a tremendous impact on customer service by interrupting the workflow of prescription fulfillment and removing pharmacy staff from dedicated responsibilities. When pharmacy staff are removed from fulfillment processes and attempt to resolve problem transactions, such as by contacting a third party including an insurance provider or a doctor, any grouping of prescriptions to be filled and/or any prioritization of prescription fulfillment can often be destroyed and can cause delayed or no prescription fulfillment. As a result, a pharmacy cannot provide service that meets customers' needs and expectations, especially at pickup when customers anticipate their prescriptions have been properly processed and are available.

As noted above, prescription fulfillment processes generally are not designed to handle problem transactions. Such processes often do not surface issues or problems early enough during prescription processing to allow sufficient time for resolution. Prescription fulfillment processes also encourage pharmacy staff to pass problems along rather than to attempt resolution because no clear protocols or procedures are provided to resolve specific issues and problems. In addition, members of pharmacy staff typically are not specifically assigned or dedicated to resolving problem transactions and are often involved in multiple tasks at different stages of prescription fulfillment. As a result, pharmacy staff can have difficulty in organizing prescriptions, maintaining priority of fulfillment and preventing unfilled prescriptions from accumulating when such tasks are performed along with efforts to resolve issues and problems. Prescription processing thereby becomes inefficient and inconsistent and can significantly impact customer service.

While pharmacy computing systems and automated workflows have greatly increased the efficiency and reliability of fulfilling customer requests, properly assigned staff and clear communication of responsibilities is required to assure proper use of those systems. Staffing is a significant cost for the operations of retail pharmacies and correctly allocating staff to the right workstations at the right times continues to be a challenge. In addition, local pharmacies and managers may not have access to the scheduling insights available through enterprise data aggregation, including the most efficient staffing models employed by similarly configured pharmacies and modeling of busy times.

SUMMARY

Various aspects for using an enterprise pharmacy information system in communication with a plurality of pharmacy workstations, particularly, using workstation interfaces to display dynamically generated work assignments are described.

One general aspect includes a system that includes a plurality of electronic workstation displays and a workstation assignment engine in network communication with the plurality of electronic workstation displays. An assignment generator is configured to: generate a first set of workstation assignments for a first set of employees during a first operation time window, and store the first set of workstation assignments in a first schedule record. A current assignment overlay is configured to: access the first schedule record; identify the plurality of electronic workstation displays corresponding to the first set of workstation assignments; and display the first set of workstation assignments on the plurality of electronic workstation displays during the first operation time window, where at least assigned workstation identifiers for an employee assigned to a selected workstation are displayed on a graphical user interface portion of a selected electronic workstation display at the selected workstation.

Implementations may include one or more of the following features. The workstation assignment engine may further include a staffing change service configured to: detect a change in coverage event for the first operation time window during the first operation time window; and select, responsive to the change in coverage event, a second set of workstation assignments. The assignment generator may be further configured to generate the second set of workstation assignments and the current assignment overlay may be further configured to replace the first set of workstation assignments on the plurality of electronic workstation displays with the second set of workstation assignments during the first operation time window and responsive to the change in coverage event. The staffing change service may be further configured to determine the change in coverage event from an electronic timesheet service configured to track employee arrivals and departures. The staffing change service may be further configured to receive a temporary change notification from a user input device associated with the plurality of electronic workstation displays. The assignment generator may be further configured to: generate at least one contingent set of workstation assignments, the at least one contingent set including the second set of workstation assignments; and store the at least one contingent set of workstation assignments in the first schedule record. The current assignment overlay may be further configured to send at least assigned workstation identifiers for an off-station employee to a mobile device associated with the off-station employee for display on a graphical user interface portion of the mobile device. The assignment generator may be further configured to use a rules engine to generate the first set of workstation assignments, where the rules engine is configured to evaluate a set of staffing rules selected from master staffing rules, regulatory compliance rules, store preference rules, employee credential rules, and employee proficiency rules. The assignment generator may be further configured to: operate in conjunction with a scheduler service for selecting specific employees for each workstation assignment; receive manager input through the scheduler service to generate the first set of workstation assignments; and automatically generate a plurality of contingent sets of workstation assignments for changes in available employees during the first operation time window. The workstation assignment engine may further include an enterprise configuration manager configured to: identify a plurality of store configuration identifiers; store a plurality of workstation responsibility card records, based on combinations of employee numbers and employee types for possible staffing configurations, organized in staffing configuration deck records; select a set of staffing configuration deck records for each store configuration identifier; and select a set of staffing rules to be applied to selecting among the set of staffing configuration deck records for each store configuration identifier. The assignment generator may be further configured to: access the set of staffing configuration deck records and the set of staffing rules for a selected store based on a store configuration identifier; and use the set of staffing configuration deck records and the set of staffing rules for selection of the first set of workstation assignments. The current assignment overlay may be further configured to display a selected workstation responsibility card record containing a workstation identifier for the selected workstation in the graphical user interface portion of the selected electronic workstation display at the selected workstation.

Another general aspect includes a computer-implemented method that includes: generating a first set of workstation assignments for a first set of employees assigned to a plurality of electronic workstation displays during a first operation time window; storing the first set of workstation assignments in a first schedule record; accessing the first schedule record; identifying the plurality of electronic workstation displays corresponding to the first set of workstation assignments; and displaying the first set of workstation assignments on the plurality of electronic workstation displays during the first operation time window, where at least assigned workstation identifiers for an employee assigned to a selected workstation are displayed on a graphical user interface portion of a selected electronic workstation display at the selected workstation.

Implementations may include one or more of the following features. The computer-implemented method may include: detecting a change in coverage event for the first operation time window during the first operation time window; selecting, responsive to the change in coverage event, a second set of workstation assignments; and replacing the first set of workstation assignments on the plurality of electronic workstation displays with the second set of workstation assignments during the first operation time window and responsive to the change in coverage event. The computer-implemented method may include determining the change in coverage event from an electronic timesheet service configured to track employee arrivals and departures. The computer-implemented method may include receiving a temporary change notification from a user input device associated with the plurality of electronic workstation displays. The computer-implemented method may include: generating at least one contingent set of workstation assignments, the at least one contingent set including the second set of workstation assignments; and storing the at least one contingent set of workstation assignments in the first schedule record. The computer-implemented method may include sending at least assigned workstation identifiers for an off-station employee to a mobile device associated with the off-station employee for display on a graphical user interface portion of the mobile device. The computer-implemented method may include evaluating, by a rules engine, a set of staffing rules selected from master staffing rules, regulatory compliance rules, store preference rules, employee credential rules, and employee proficiency rules, where generating the first set of workstation assignments is responsive to the evaluation of the set of staffing rules. The computer-implemented method may include: receiving manager input through a scheduler service; selecting specific employees for each workstation assignment in the first set of workstation assignments; and automatically generating a plurality of contingent sets of workstation assignments for changes in available employees during the first operation time window. The computer-implemented method may include: identifying a plurality of store configuration identifiers; storing a plurality of workstation responsibility card records, based on combinations of employee numbers and employee types for possible staffing configurations, organized in staffing configuration deck records; selecting a set of staffing configuration deck records for each store configuration identifier; selecting a set of staffing rules to be applied to selecting among the set of staffing configuration deck records for each store configuration identifier; accessing the set of staffing configuration deck records and the set of staffing rules for a selected store based on a store configuration identifier, where generating the first set of workstation assignments uses the set of staffing configuration deck records and the set of staffing rules to select the first set of workstation assignments; and displaying a selected workstation responsibility card record containing a workstation identifier for the selected workstation in the graphical user interface portion of the selected electronic workstation display at the selected workstation.

Another general aspect includes a pharmacy workstation that includes at least one processor, at least one memory, a network interface for network communication with a workstation assignment engine, and an electronic workstation display having a graphical user interface configured to: display a pharmacy workstation interface configured for completing workstation tasks during a first operation time window; display a current assignment overlay that obscures at least a portion of the pharmacy workstation interface during the first operation time window to display at least assigned workstation identifiers for an employee assigned to the pharmacy workstation in a first set of workstation assignments; and display, responsive to a change in coverage event during the first operation time window, an updated current assignment overlay to display at least updated assigned workstation identifiers for the employee assigned to the pharmacy workstation in a second set of workstation assignments.

Implementations may include one or more of the following features. The first set of workstation assignments may be based on a first set of workstation responsibility card records organized in a first staffing configuration deck record corresponding to a combination of employee numbers and employee types for a first staffing configuration. The second set of workstation assignments may be based on a second set of workstation responsibility card records for a second staffing configuration deck record corresponding to a different combination of employee numbers and employee types for a second staffing configuration. The current assignment overlay may include a first workstation responsibility card from the first set of workstation responsibility card records containing a workstation identifier for the pharmacy workstation and the updated current assignment overlay may include a second workstation responsibility card from the second set of workstation responsibility card records containing the workstation identifier for the pharmacy workstation.

The various embodiments advantageously apply teachings of pharmacy information systems utilizing distributed networks of workstation computing systems with graphical displays to improve the functionality of such computer systems. The various embodiments include operations to overcome or at least reduce the issues in the previous pharmacy information systems discussed above and, accordingly, are more reliable and/or efficient than other computing networks. That is, the various embodiments disclosed herein include hardware and/or software with functionality to improve the efficient distribution and display of work assignments and dynamic updates thereof based on preconfigured staffing configuration data structures and rules logic for selecting workstation configurations and staff assignments. Accordingly, the embodiments disclosed herein provide various improvements to enterprise data systems and/or retail workstations, particularly for pharmacy information systems.

It should be understood that language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation, in the figures of the accompanying drawings in which like reference numerals are used to refer to similar elements.

DETAILED DESCRIPTION

Figure 1:
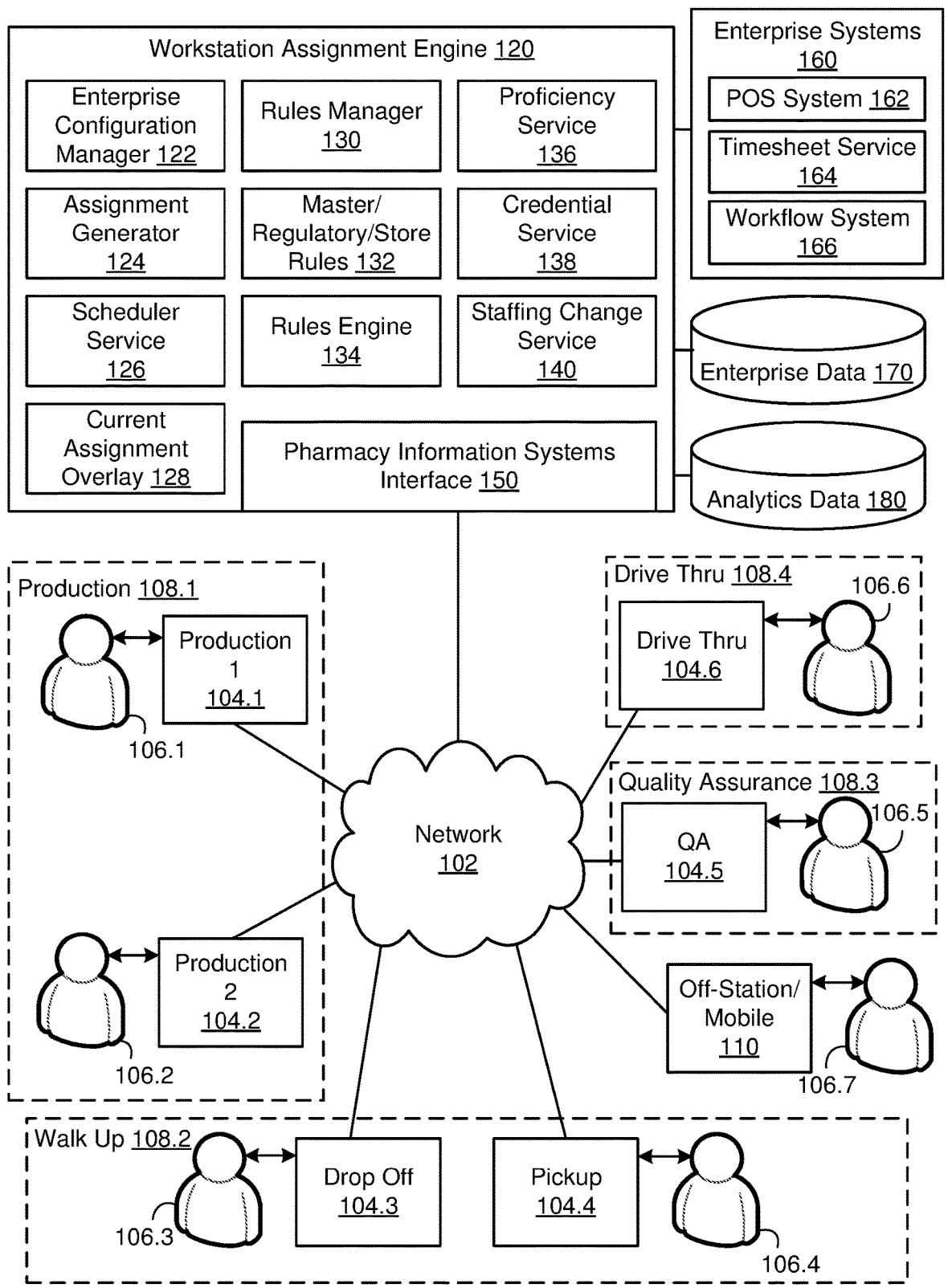
FIG. 1 is a block diagram of an example pharmacy enterprise information system, including an example set of retail pharmacy workstations.

With reference to the figures, reference numbers may be used to refer to components found in any of the figures, regardless whether those reference numbers are shown in the figure being described. Further, where a reference number includes a decimal referring to one of multiple similar components (e.g., component 000.1, 000.2, and 000.3), the reference number may be used without the decimal to refer to one or all of the similar components.

A pharmacy or similar workspace may include multiple workstations for processing and fulfilling drug prescriptions wherein one or more workstations perform one or more stages involved in processing prescriptions. Each workstation is designated, and, optionally, is configured, to accomplish one or more tasks. Workstation tasks can be defined in terms of the roles and responsibilities, as well as the skill levels required, of persons who staff each workstation. Further, workstation tasks can be further defined to limit or focus pharmacy staff-customer interfaces whereby a designated workstation is limited or focused to one or more specific pharmacy-customer interfaces such as, for instance, walk-in drop-off workstations can be limited to interacting with walk-in customers, while drive-thru workstations can be limited to interacting with drive-thru customers. In addition, definition of workstation tasks can be directed to limiting staff to a single or primary pharmacy customer interface of a workstation to ensure effective customer communication and efficient workflow.

The designated workstations and defined tasks help to create a stage-by-stage process or a compartmentalized workflow whereby each processing stage is handled and/or completed at one or more workstations by one or more staff persons having the requisite skill level, e.g., registered pharmacist (RPh), certified or otherwise trained technician (CT), a customer support associate (CSA) or other support person. In addition, the workstations and tasks are so defined to help to permit early detection and resolution of issues or problems that can occur during processing. Further, the defined workstations and tasks help to ensure pharmacy communication with customers concerning prescription problems and help a pharmacy to provide customers with relatively accurate prescription pick-up times that meet customers' needs and expectations. In part, the invention uses real-time prioritization with respect to prescription fulfillment whereby the actual times when fulfilled prescriptions are promised for customer pick-up are used to manage and to prioritize pharmacy workflow. Real-time prioritization can further take into account whether a customer will wait for his/her prescription to be fulfilled or will return to the pharmacy at a later time to pick-up the fulfilled prescription in order to further manage and prioritize workflow. The system and methods according to the invention thereby provide an efficient and streamlined process for fulfilling drug prescriptions in a timely manner, while minimizing/eliminating the impact of issues and problems associated with processing drug prescriptions.

Typically, processing prescriptions in a retail pharmacy include one or more stages of drop-off or submitting a drug prescription to a pharmacy, data intake or obtaining prescription and customer information, production or dispensing drugs according to prescriptions, quality assurance or verifying that appropriate drugs have been dispensed, and pick-up or providing the fulfilled prescription to a customer or an agent for a customer. Within each of these stages, a number of complex issues and problems can arise during processing of drug prescriptions that can significantly affect the quality and the efficiency with which prescriptions are fulfilled and dispensed to customers. Pharmacy workflow systems have been implemented to address many of these issues and problems and to resolve such issues and problems at early stages of processing to help to ensure efficient and timely prescription fulfillment and to enhance customer service.

As further context, a customer typically submits a drug prescription to a pharmacy, e.g., by hand, by telephone, by leaving a voice mail message on a pharmacy voice response system, by faxing the prescription to the pharmacy, and/or by the customer's prescriber/doctor telephoning or faxing the pharmacy to "call-in" the prescription. After submission of the prescription to the pharmacy, communication or contact between these parties is typically terminated. The prescription then proceeds from drop-off to one or more data intake stages whereby a pharmacy obtains prescription and customer information, e.g., health insurance information.

Stages of data intake typically involve at least four general areas of prescription processing, prior to stages of production, during which complex issues and problems can occur that often require resolution before a prescription can be further processed and successfully fulfilled. These areas include entering data related to a drug prescription and customer information into a pharmacy's information processing system, e.g., a networked computer system comprised of one or more operatively connected computers, checking a pharmacy inventory for stock, conducting a drug utilization report or DUR check, and performing insurance adjudication review. Issues and problems that arise during data intake, inventory check, DUR check, and insurance adjudication review can require pharmacy personnel to take several steps and to make considerable effort to resolve before prescriptions can be fulfilled. Even with the guidance of an automated pharmacy workflow system, resolution can take from a few minutes up to several days and can involve a number of pharmacy personnel.

For example, when a pharmacy obtains and enters a prescription into a pharmacy's processing system, the system can provide feedback that the prescription cannot be refilled. A "no refill" status must be resolved before the prescription can be further processed and filled. A number of steps are typically undertaken to resolve this issue including identifying the prescription to alert pharmacy personnel that a prescriber/doctor who provided the original prescription must be contacted. Thereafter, guided by prompts from the workflow system, attempts may be made to contact the prescriber/doctor. An initial attempt to contact the prescriber/doctor may not be successful and the prescription is identified as a "doctor call-back", which requires periodically contacting the prescriber/doctor until a decision is obtained from the prescriber/doctor. In the event the prescriber/doctor denies the refill prescription, the prescription is identified as a "denied" prescription. Without an established protocol and staff specifically assigned to handle "no refills", such prescriptions can often end up languishing at the data intake stages, which can cause prescriptions to be filled late or not at all.

A pharmacy inventory may be checked to confirm whether sufficient volume is currently in inventory to fulfill the prescription. Typically, a pharmacy's information processing system will indicate whether a drug inventory is sufficient, insufficient, or out-of-stock. In the event the system indicates the stock is sufficient, the prescription is filled accordingly. In the event the system indicates an insufficient stock or out-of-stock status, the prescription is not fulfilled or only partially fulfilled. The workflow system may generate notifications and/or subsequent actions to verify stock, contact the customer, initiate reorders, contact another pharmacy, or take further remedial action on an automated bases or with the assistance of one or more staff.

Each prescription may undergo a DUR check. After or in conjunction with a pharmacy entering prescription information into its processing system at data intake stages, the pharmacy typically conducts a DUR review to ensure proper drug dose, etc. and to confirm whether any adverse drug interactions may exist between the prescribed drug and any other drugs a customer taking. In the event a DUR check registers an issue, e.g., the pharmacy's processing system flags the issue, e.g., a negative DUR such as an incorrect dose or an adverse drug interaction, a registered pharmacist (RPh) must become involved to review the DUR and to either override the issue or negative DUR in the pharmacy's system or contact a prescriber/doctor for further consultation. Typically, an RPh's involvement occurs during the data intake stages and causes the RPh to be drawn from his/her primary responsibilities, e.g., production and/or quality assurance, which can result in delays in dispensing prescriptions.

Insurance adjudication review can cause complex issues that impact processing of prescriptions. A customer's insurance can reject a prescription for a number of reasons including policy cancellation, no refill authorized or prior authorization is required from an insurance provider. Upon rejection, pharmacy personnel must review reasons for insurance rejection and attempt to overcome such problems either by overriding the insurance rejection through a pharmacy's processing system or resolving issues causing the rejection. Often insurance rejections are caused by minor issues, such as an incorrect name spelling, birth date, or insurance policy number, and can be readily resolved by any staff person by overriding the pharmacy's processing system. Other insurance problems are more complex or difficult to resolve and can only be handled by contacting a third party, such as a prescriber/doctor, who wrote the prescription, or an insurance provider, to identify the causes for rejection.

In retail pharmacies, pharmacy staff, including pharmacists, technicians, customer support assistants, and/or other staff, may be assigned to physical workstations, generally designated by a workspace area (counter, desk, table, cubicle, cart, etc.) configured for one or more tasks and including at least one workstation computing device. Workstation computing devices may include general purpose computers and/or more specialized computing devices including at least one electronic workstation display and at least one user input device, such as keyboard, mouse, touchscreen, etc. Workstation computing devices may be configured for a specific workstation task and/or provide menu access to a plurality of workstation functions, sometimes organized by workstation type, task, staff responsibilities, and/or general functions. In some embodiments, workstation computing devices may be connected via a network to local, remote, or enterprise information systems for data retrieval, processing, and/or one or more pharmacy or retail applications.

As shown in FIG. 1, retail pharmacy information system 100 may be configured to enable a plurality of workstation computing systems 104 to communicate over network 102 to a workstation assignment engine 120 and other enterprise computing resources, such as enterprise systems 160, enterprise data store 170, and analytics data store 180. In the example shown, workstation computing systems 104 are allocated to different physical workstations 108 for use by staff 106. Production workstation 108.1 includes two production workstation computing systems 104.1 and 104.2 for use by staff 106.1 and 106.2. Walk-up workstation 108.2 includes drop off workstation computing system 104.3 and pickup workstation computing system 104.4 for use by staff 106.3 and 106.4. Quality assurance workstation 108.3 includes quality assurance workstation 104.5 for use by staff 106.5. Drive thru workstation 108.4 includes drive thru workstation 104.6 for use by staff 106.6. In some embodiments, network 102 may connect to one or more off-station or mobile computing devices 110 used by staff, such as staff 106.7, when off-station employees are working on tasks away from the designated workstation computing systems 104. For example, a tablet or similar computing device may be configured for use on one or more off-station tasks and/or staff may have a personal or corporate smartphone that they carry with them when off-station. These mobile computing devices may be equipped with an application for accessing and/or receiving notifications from workstation assignment engine 120 and/or other enterprise computing resources.

In some embodiments, workstation assignment engine 120 may enable dynamic generation and reconfiguration of workstation assignments based on real-time information, such as staff members signing in or out, unscheduled tasks, or interruptions. In some embodiments, system-level configurations may enable an enterprise to implement policy-based rules or logic to enforce regulatory staffing requirements, enterprise best practices, and/or human resource policies. Workstation assignment engine 120 may act as a gateway for communication with other enterprise systems and data resources, such as enterprise information systems 160, enterprise data stores 170 and/or analytics data stores 180. These enterprise systems may enable workstation assignment engine 120 and related applications or interfaces displayed on the electronic workstation displays of workstation computing systems 104 at various workstation locations 108 to send and receive data related to configuration, modification, and display of workstation assignment cards. Workstation assignment engine 120 may integrate with human resource systems in enterprise systems 160, such as electronic timesheet service 164. This integration may include the ability to send schedule feeds to scheduler service 126 of workstation assignment engine 120, the ability to send real-time punch-in and out feeds to staffing change service 140 of workstation assignment engine 120, and the ability to send the pharmacy job codes at the store level to the assignment generator 124 of workstation assignment engine 120.

In some embodiments, workstation assignment engine 120 may be hosted on one or more servers comprised of a plurality of processor, memory, data storage, network, and other resources configured to execute one or more software and/or hardware modules. For example, workstation assignment engine 120 may be hosted as an application, group of applications, and/or functions within one or more other enterprise pharmacy management applications hosted in an enterprise or cloud computing architecture. Computing resources hosting workstation assignment engine 120 may include one or more components of or interfaces to enterprise information systems 160, enterprise data stores 170, and/analytics data stores 180. Workstations assignment engine 120 may include a pharmacy information systems interface 150. For example, pharmacy information systems interface 150 may include physical, transport, data, protocol, and security interfaces for communicating with other components of retail pharmacy information system 100. In some embodiments, pharmacy information systems interface 150 may be configured to use internet-based communication protocols to establish network connections through network 102 to workstation computing systems 104, as well as enterprise systems 160, enterprise data stores 170, and/or analytics data 180.

Workstation assignment engine 120 may include an interface protocol and set of functions, parameters, and data structures for managing automated workstation assignments for retail pharmacies based on an enterprise pharmacy information system. In some embodiments, workstation assignment engine 120 may include a plurality of hardware and/or software modules configured to use a processor and memory to execute defined operations of workstation assignment engine 120. For example, workstation assignment engine 120 may include an enterprise configuration manager 122, an assignment generator 124, a scheduler service 126, a current assignment overlay generator 128, a rules manager 130, a master/regulatory/store rules set 134, a rules engine 134, a proficiency service 136, a credential service 138, and a staffing change service 140.

Enterprise configuration manager 122 may include interfaces and supporting functions and data structures to provide centralized control of workstations assignment engine availability, functions, and configurations available to specific regions or stores. For example, enterprise configuration manager 122 may include a management dashboard, such as a graphical user interface, configured for navigating a plurality of store configurations. In some embodiments, the store configurations may be stored independently in configuration files, database entries, or similar data structures and may be organized according to various hierarchies or classification schemes, such as store location, store configuration identifier, store services/departments, etc. For example, enterprise configuration manager 122 may be configured to manage responsibility or workstation cards and configuration decks to the store level, such as sending specific cards or decks configured for a specific store. Some parameters in enterprise configuration manager 122 may be managed based on hierarchies, tags, or similar classifications associated with the stores to enable, for example, all stores in a state (or other geographical designation) or all stores with a particular store configuration to have parameter set or changes as a group. In some embodiments, enterprise configuration manager 122 may interact with rules manager 130 and/or master/regulator/store rules sets to configure the rule sets available to individual stores and/or groups. In some embodiments, enterprise configuration manager 122 may control access to assignment generator 124, scheduler service 126, current assignment overlay 128, proficiency service 136, credential service 138, and/or staffing service 140 to enable, disable, or otherwise configure those services for use by retail stores. Master, state, and store level switches to turn on or off workstation assignment functions or features may be available for managing store access via a regulatory and/or corporate route, such as through enterprise configuration manager 122. Each individual functionality of the workstation assignment engine may be managed at the master, store, and state/regulatory level via the regulatory and/or corporate system access routes. For example, configuration settings to turn on/off specific workstation assignment cards at a store/state level based on various constraints, such as job code constraints, technician to pharmacist ratios, etc.

Assignment generator 124 may include interfaces and supporting functions for enabling an automated workstation assignment generator for the retail pharmacies. For example, assignment generator 124 may use staffing data in enterprise data stores 170 and/or timesheet service 164 to populate a set of work assignments for each shift and/or rotation of a retail pharmacy. In some embodiments, population of colleagues into a set of assignment cards may be done automatically by assignment generator 124. Jurisdiction and other rules may be applied by assignment generator 124 (using rules engine 134) when selecting staff for specific workstation assignments, such as based on job code, with different results in different jurisdictions (e.g. any technician with job code 123456 in OH should not be placed at Drop Off, but technicians with the same job code could be placed at Drop Off in Rhode Island). In some embodiments, assignment generator 124 may include logic for real-time adjustment of workstation assignments based on staffing and task changes received through timesheet service 164 and/or staffing change service 140. For example, assignment generator 124 may use a current configuration of workstation assignments, change information (staff or task changes), and rules engine 134 to evaluate a set logical rules for adjusting the work assignments and providing updated workstation assignments for display through current assignment overlay generator 128.

Scheduler service 126 may include interfaces and supporting functions for enabling assignment engine 124 to assist (or automate) staff scheduling for the retail pharmacy. For example, scheduler service 126 may integrate with a scheduling application used by pharmacy managers to schedule their staff for the coming week, month, or other time period. The scheduling application may include a pool of staff organized by titles or credentials and a calendar with identified shifts for the manager to assign staff to. Scheduler service 126 may be configured to generate staffing models based on ratios of different staff types, such as pharmacists and pharmacy technicians. Scheduler service 126 may use assignment generator 124 to automatically generate and initial staffing configuration with staff assignments and populate the staffing application with those staff assignments. Scheduler service 126 may further support modification of the automatically generated assignments by the pharmacy manager and/or an iterative process for evaluating different staffing configurations and staff assignments. In some embodiments, a pharmacy scheduler may send schedules and proficiencies (i.e. rating scales at each workstation) to the workstation assignment engine for use in populating assignment cards.

Current assignment overlay generator 128 may include interfaces and supporting functions for enabling workstation assignment engine 120 to publish staff assignments as a graphical user interface element across workstation computing systems 104. For example, current assignment overlay generator 128 may format a pop-up or overlay user interface element for all colleagues to view at each pharmacy terminal each time there is a change in the number of colleagues and at each scheduled rotation (e.g. every two hours). In some embodiments, the current assignment overlay GUI may include a set of graphical card elements that identify each workstation and the staff member(s) assigned to that station. The graphical card elements may also include off-station task assignments. The current assignment overlay GUI and/or other workstation assignment engine functions may also be accessible via a hotkey and/or navigation option at each pharmacy terminal. The current assignment overlay GUI and/or other navigation options may enable an expanded view or new window on the pharmacy terminals to be able to view the assignment cards for the current timeslot and/or navigate other assignment card sets for other time periods in the day. This may include the ability to display, hide, and edit the full day schedule in advance. In some embodiments, the current assignment overlay GUI is a pop-up over a pharmacy information system interface, such as a pharmacy task or workflow manager supported by enterprise workflow system 166.

Rules manager 130 may include interfaces and supporting functions for enabling a user of workstation assignment engine 120 to add, modify, and delete logical rules used by assignment generator 124 and rules engine 134 to determine staffing assignments for scheduler service 126 and/or staffing change service 140. For example, rules manager 130 may include a graphical user interface for organizing individual logical rules and/or rule sets and an editor for selectively adding, modifying, and deleting logical rules based on a set of rule parameters and/or a rule definition language. Rules manager 130 may store rules and rule sets in master/regulatory/store rules 132.

Master, regulatory, and store rules may be configured and stored through rules manager 130 and executed via a rule execution service, such as rules engine 134. Master/regulatory/store rules 132 may include a rules data store, file, database, table, and/or other data structure for storing the set(s) of rules used by workstation assignment engine 120. Master staffing rules may include a set of rules defined at an enterprise level for all pharmacies, such as fundamental parameters of assignment generator 124 and/or workstation configuration or assignment rules enforcing enterprise-wide policies. Regulatory compliance rules may include one or more sets of rules based on different jurisdictions, such as required staffing levels, ratios, and/or qualifications for specific assignments that may be required by different state or local regulations. Store preference rules may include one or more sets of rules defined for specific store types, configurations, or other factors. In some embodiments, store preference rules may include rules defined for individual stores by corporate exception or enabling some local customization of how assignment generator 124 operates.

Rules engine 134 may include interfaces and supporting functions for run-time evaluation of rules sets from master/regulatory/store rules 132. For example, assignment generator 124 may invoke rules engine 134 to evaluate workstation, staff, and other inputs provided by scheduler service 126 and/or staffing change service 140 according to the set of master, regulatory, and store rules that apply to a specific retail pharmacy and set of parameters for generating new staffing assignments. Rules engine 134 may include logic for processing rules parameters based on a rule definition language that maps received assignment parameter sets to a staff assignment output, such as a set of staffing decks and cards, with specific staff assigned to specific workstations.

Proficiency service 136 and credential service 138 may include interfaces and supporting functions for providing additional criteria for assignment generator 124 and rules engine 134 to use for making staffing assignments. For example, workstation assignment engine 120 may interact with a pharmacy data warehouse, such as enterprise data 170, to access credential and/or proficiency data for the pharmacy staff. Credential information for use in employee credential rules may include licensing, certifications, professional degrees, professional memberships, regulatory compliance, and other professional credentials that may determine whether staff can perform specific tasks or staff particular workstations. For example, a pharmacy may include a clinical station for administering flu shots, other vaccines, health screenings, and the like that may require specific credentials for staff. Proficiency information for use in employee proficiency rules may include identification and/or rating of specific tasks and workstation assignments for various staff. For example, a human resources management system may include training data and/or employee ratings (self-rating, manager rating, automated rating logic, etc.) that identify staff competencies. In some embodiments, proficiency service 136 may support an interface for pharmacy managers or others to rate employee proficiency at the various workstation assignments based on a high, medium, low rating system. More complex proficiency rating systems are also possible, including numerical and system-generated rankings of staff performance at various tasks. Assignment generator 124 may use proficiency service 136 and/or credential service 138 to assure that workstations and tasks are not assigned to staff who lack the necessary credentials and/or proficiencies for those tasks and/or prioritize assignment of staff with higher ratings for critical assignments and/or the busiest timeslots.

Staffing change service 140 may include interfaces and supporting functions for detecting changes in the staff present and/or assigned to workstations or tasks during pharmacy operation. For example, some pharmacy terminals may be configured as point-of-sale (POS) systems that include employee clock-in and clock-out logging functions. POS computing systems may interface with enterprise POS system 162 for sales transactions and timesheet service 164 for enabling employees to clock-in and clock-out. Pharmacy computing systems 104 may send clock-in and clock-out times to staffing change service 140 in real-time to trigger reconfiguration of assignment cards based on the resulting staffing levels or change in personnel and proficiencies. For example, assigned staff may be delayed or absent for a shift and staffing change service 140 may detect that the staff assigned in the current assignment are not present and assignment generator 124 may need to determine a new set of assignments based on the reduced staff level.

In some embodiments, staffing change service 140 may also support backup requests and/or temporary staffing changes to enable unscheduled interruptions, breaks, or tasks that arise during pharmacy operations. For example, pharmacy computing systems may include a feature for requesting backup, such as the ability for staff working at customer facing workstations to ask for backup support through staffing change service 140, possibly triggering a reconfiguration of workstation assignments, in addition to providing notification to other team members. A backup notification window may be populated or displayed on all other relevant pharmacy terminals. In addition to backup requests, staffing change service 140 may support manual override of current assignments to support flexibility in pharmacy operations. For example, the pharmacist or pharmacy manager may be able to initiate a reassignment of staff between workstations and/or off-station tasks. In some embodiments, a callout will capture the credential of the person initiating the override when there is a manual override. Example data elements captured may include override stations (the workstations or task assignments changed), modification reasons, the staff who overrides, job codes, date, time, etc.

Figure 2:
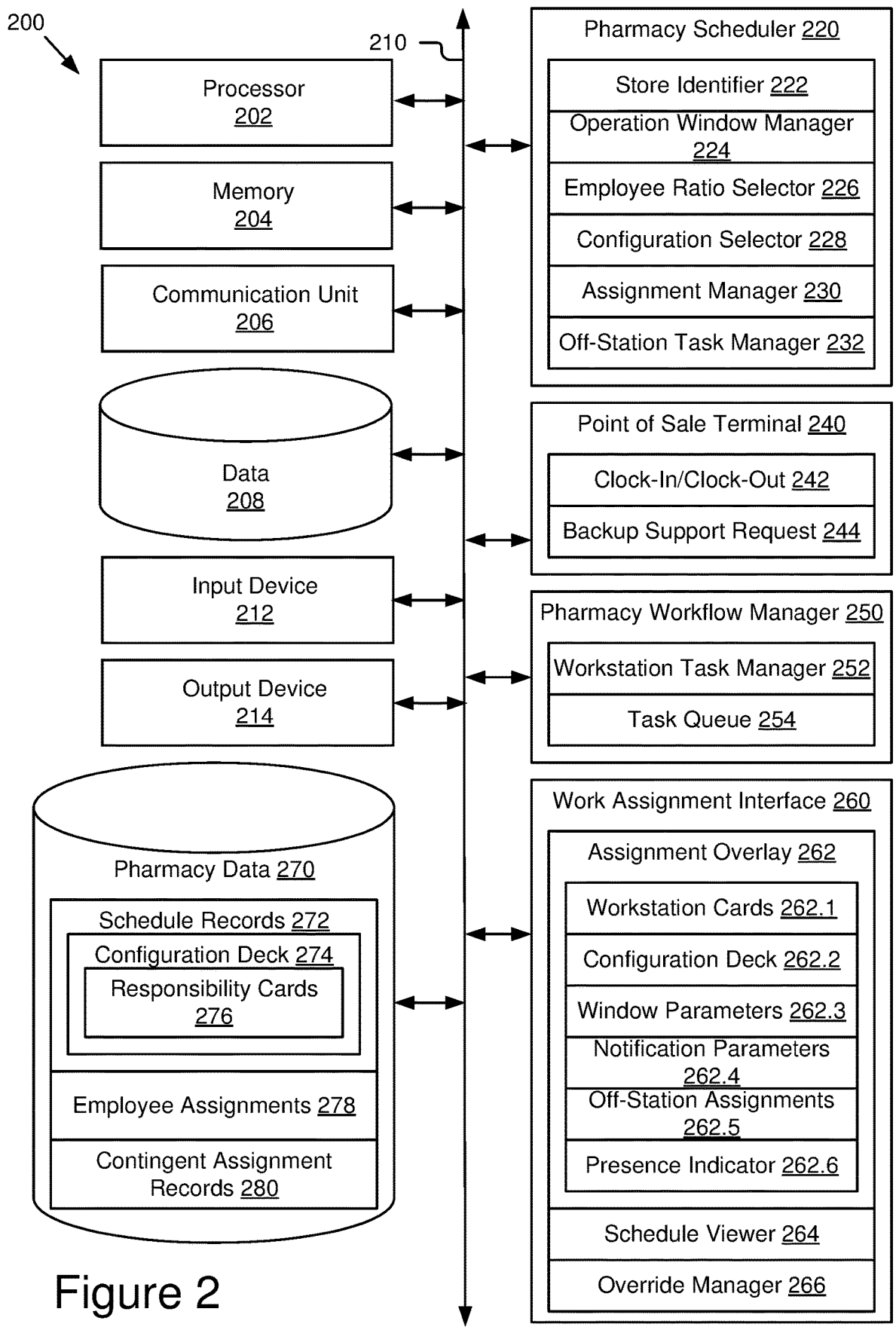
FIG. 2 is a block diagram of an example pharmacy computing system, such as a workstation computing system.

FIG. 2 schematically shows selected modules of one or more pharmacy computing systems configured to use workstation assignment engine 120 to dynamically allocate work assignments during pharmacy operation. Pharmacy computing system 200 may be configured as one or more workstation terminals, such as point-of-sale systems, prescription processing workflow systems, etc. in network communication with one another and/or an enterprise pharmacy information system. In some embodiments, pharmacy computing system 200 may include one or more of the pharmacy computing systems 104 in the retail pharmacy computing system 100 of FIG. 1. The workstation assignment engine may connect with each pharmacy computing system 200 and all enterprise systems bi-directionally and share the real-time card assignments and/or underlying data based on algorithms or APIs defined with each such system. Pharmacy computing system 200 may also interface directly with other enterprise or local data systems, such as a pharmacy scheduler application and/or a pharmacy task manager application, and this data may be provided from the pharmacy terminals to the workstation assignment engine or directly by the supporting enterprise systems.

One or more pharmacy terminals may be configured for accessing the workstation assignment engine and various related features. Card assignment configurations may be generated by the workstation assignment engine for display on pharmacy terminals. The workstation assignment engine may create a dynamic view of the card assignments with automatically integrates clock-in times, clock-out times, and the schedules and proficiencies of the staff available. For example, the workstation assignment engine may generate a set of assignment or configuration decks or templates and be able to assign specific assignment deck versions at a store level. In some configurations, different configuration decks may be available for different jurisdictions (e.g. CA, NY, FL, etc.) and different store configurations (drive thru, no drive thru, clinic, etc.), based on jurisdiction identifiers and store configuration identifiers. Each version may have a large number of timeslot configurations based on technician to pharmacist ratios, staffing, and projected priority for different stations (based on historic business model). Workstation activities associated with each card may be configurable at the store-level. Colleague named may be displayed with a job code and/or title when populating responsibility cards in the configuration decks for use in schedule and dynamic reassignment.

As depicted, the computing device 200 may include a processor 202, a memory 204, a communication unit 206, a data store 208, an input device 212, and an output device 214, which may be communicatively coupled by a communication bus 210. Computing device 200 depicted in FIG. 2 is provided by way of example and it should be understood that it may take other forms and include additional or fewer components without departing from the scope of the present disclosure. For instance, various components of the computing device may be coupled for communication using a variety of communication protocols and/or technologies including, for instance, communication buses, software communication mechanisms, computer networks, etc. While not shown, computing device 200 may include various operating systems, sensors, additional processors, peripheral devices (e.g. label printer, bar code scanner, etc.), and other physical configurations. Processor 202, memory 204, communication unit 206, etc., are representative of one or more of these components. In some embodiments, one or more components of computing device 200 may be accessible to computing device 200 via communication unit 206 and one or more network interfaces, such as network communication via network 102.

Processor 202 may execute software instructions by performing various input, logical, and/or mathematical operations. Processor 202 may have various computing architectures to manipulate data signals (e.g., CISC, RISC, etc.). Processor 202 may be physical and/or virtual, and may include a single core or plurality of processing units and/or cores. In some implementations, processor 202 may be coupled to memory 204 via bus 210 to access data and instructions therefrom and store data therein. Bus 210 may couple processor 202 to the other components of the computing device 200 including, for example, memory 204, communication unit 206, data store 208, input device 212, and output device 214.

Memory 204 may store and provide data access to the other components of computing device 200. Memory 204 may be included in a single memory device or a plurality of memory devices. In some implementations, memory 204 may store instructions and/or data that may be executed by the processor 202. For example, memory 204 may store instructions and data, including, for example, an operating system, hardware drivers, other software applications, databases, etc. which may implement the techniques described herein. Memory 204 may be coupled to bus 210 for communication with processor 202 and the other components of computing device 200. Memory 204 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with processor 202. In some implementations, memory 204 may include one or more of volatile memory and non-volatile memory (e.g., RAM, ROM, hard disk, optical disk, etc.). It should be understood that memory 204 may be a single device or may include multiple types of devices and configurations. In some embodiments, memory 204 may instantiate and/or store pharmacy scheduler 220, point of sale terminal 240, pharmacy workflow manager 250, and/or work assignment interface 260 for execution by processor 202.

Communication unit 206 may include one or more interface devices (I/F) for wired and wireless connectivity among the components of the system 100. For instance, the communication unit 206 may include, but is not limited to, various types of known connectivity and interface options. In some embodiments, communication unit 206 may include a network interface, such as a network adapter, for communicating via a wired and/or wireless network 102 with other computing resources, devices, or systems. Communication unit 206 may be coupled to the other components of computing device 200 via bus 210. Communication unit 206 can provide other connections to the network 102 and to other entities of system 100 using various standard communication protocols.

Data store 208 may include information sources for storing and providing access to data. In some implementations, data store 208 may store data associated with a database management system (DBMS) operable on the computing device 200. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations. The data stored by data store 208 may be organized and queried using various criteria including any type of data stored by them. Data store 208 may include data tables, databases, data files, data objects, or other organized collections of data. Data store 208 may be included in computing device 200 or in another computing system and/or storage system distinct from but coupled to or accessible by computing device 200. Data stores 208 can include one or more non-transitory computer-readable mediums for storing the data. In some implementations, data stores 208 may be incorporated with memory 204 or may be distinct therefrom.

Bus 210 can include a communication bus for transferring data between components of a computing device or between computing devices, a network bus system including network 102 or portions thereof, a processor mesh, a combination thereof, etc. In some implementations, various components operating on the computing device 200 (operating systems, device drivers, etc.) may cooperate and communicate via a communication mechanism included in or implemented in association with bus 210. The software communication mechanism can include and/or facilitate, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

Input device 212 may include any device for inputting information into computing device 200. In some implementations, input device 212 may include one or more peripheral devices. For example, input device 212 may include a keyboard, a pointing device, microphone, an image/video capture device (e.g., camera), a touch-screen display integrated with the output device 214, and other user input devices. Output device 214 may be any device capable of outputting information from the computing device 200. The output device 214 may include one or more of a display (LCD, OLED, etc.), a printer, a haptic device, audio reproduction device, touch-screen display, a remote computing device, etc. In some implementations, output device 214 may include a display which may display electronic images and data output by a processor of the computing device 200 for presentation to a user, such as the processor 202 or another dedicated processor. For example, output device 214 may include a monitor or other display to provide a graphical user interface between a user, such as pharmacy staff, and computing device 200. In some embodiments, each workstation computing system may include a monitor to provide a graphical user interface for displaying workstation assignment notifications and interfaces.

Components 204, 206, 208, 212, and/or 214 may be communicatively coupled by bus 210 and/or processor 202 to one another and/or the other components of computing device 200. In some implementations, components 204, 206, 208, 212, and/or 214 may include computer logic (e.g., software logic, hardware logic, etc.) executable by processor 202 to provide their acts and/or functionality. In any of the foregoing implementations, these components 204, 206, 208, 212, and/or 214 may be adapted for cooperation and communication with processor 202 and the other components of the computing device 200.

Computing system 200 may include or have access to one or more databases and/or specialized data stores, such as pharmacy data store 270. Databases may include one or more data structures for storing, retrieving, indexing, searching, filtering, etc. of structured and/or unstructured data elements. Pharmacy data store 270 and/or other databases or data structures may be maintained and managed in separate computing systems, such as storage nodes, with separate communication, processor, memory, and other computing resources and accessed by computing device 200 through data access protocols. In some embodiments, some or all contents of pharmacy data store 270 may be stored remotely in an enterprise pharmacy information system, such as in enterprise data store 170 in FIG. 1.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

Pharmacy computing system 200 may include a plurality of modules or subsystems that are stored and/or instantiated in memory 204 for execution by processor 202. For example, memory 204 may include pharmacy scheduler 220 configured to determine and manage a schedule of future dates and time windows (workdays, shifts, rotations, etc.). Memory 204 may include POS terminal 240 configured for providing POS functions and transactions supported by an enterprise POS system, including functions related to staffing. Memory 204 may include a pharmacy workflow manager 250 configured for supporting workstation tasks related to prescription fulfillment and other pharmacy functions. Memory 204 may include a work assignment interface 260 configured to provide notification and management of work assignments during pharmacy operations. In some embodiments, pharmacy scheduler 220, pharmacy workflow manager 250, and/or workstation assignment interface 260 may be integrated into point of sale terminal 240 and/or managed as separate libraries or background processes (e.g. daemon) through an API or other interface.

Pharmacy scheduler 220 may include an interface protocol or set of functions, parameters, and data structures for generating, modifying, and otherwise managing a daily staffing schedule for a retail pharmacy. For example, pharmacy scheduler 220 may include functions for identifying future time periods, such as days, weeks, months, etc., organizing staffing increments, such as shifts and/or rotations, and assignment specific employees to those shifts and days.

In some embodiments, pharmacy scheduler 220 helps a pharmacy to predict the number of staff that will be required for each skill level for a given day and for specific hours of the day and to create from such predictions staffing schedules that help to meet and optimize a predicted workflow. Pharmacy scheduler 220 may use store-specific data and chainwide data from a multiple of stores that are tracked during pharmacy operation to determine staffing needs. For example, pharmacy scheduler may use store-specific and/or chainwide data that accounts for and helps to predict staffing needs required to recognize and to resolve issues and problems associated with drug prescription fulfillment at early stages of processing. For instance, store-specific data and chainwide data can be used to predict the timing of a pharmacy activity in terms of specific hours of business day and specific days of the week, and to further predict the volume of such activity during these times. Pharmacy scheduler 220 can be configured to convert the predicted pharmacy activities into estimated numbers of total staff required and staff required at each skill level, e.g., registered pharmacist, certified or otherwise trained technician, customer support associate, or support staff, for specific hours of a business day and specific days of the week to carry out the predicted pharmacy activities. An assignment generator, such as assignment generator 124 may then calculate a recommended "skeleton" staffing schedule for a period of time, e.g., one week, two weeks or a month, from the estimated numbers of staff required. The skeleton staffing schedule may recommend the number of staff at each skill level, e.g., the number of pharmacists, technicians or support staff, to be scheduled for each hour and each day based upon the predicted pharmacy activities and the estimated numbers of staff required at each skill level. The number of staff of each level may be referred to as a staffing or employee ratio for any given operation window (shift, rotation, etc.). In some embodiments, pharmacy scheduler 220 may compare the skeleton staffing schedule for a period of time, e.g., one week, to an existing staffing schedule for a similar period of time, e.g., a prior week. Pharmacy scheduler 220 may generate from the comparison of the skeleton and existing schedules, a gap/surplus report that summarizes the staffing surpluses and deficiencies for each hour of each day to be scheduled. In some embodiments, pharmacy scheduler 220 may produce a number of possible staffing configurations by generating multiple skeleton staffing schedules for the same period of time and allowing a pharmacy manager to select a primary or preferred schedule. Pharmacy scheduler 220 may enable a user or scheduler, such as a pharmacy manager, to adjust a staffing schedule by removing or minimizing surpluses and/or deficiencies identified in the gap/surplus report to meet the recommended staffing for each hour, and to produce a model staffing schedule from the adjusted gap/surplus report from which staff are scheduled. Pharmacy scheduler 220 may be configured to store the schedule data generated in schedule records 272, employee assignments 278, and/or contingent assignment records 280 in pharmacy data store 270.

In some embodiments, pharmacy scheduler 220 may include a plurality of hardware and/or software modules configured to use processor 202 and memory 204 to handle or manage defined operations of pharmacy scheduler 220. For example, pharmacy scheduler 220 may include a store identifier 222, an operation window manager 224, an employee ratio selector 226, a configuration selector 228, an assignment manager 230.

Store identifier 222 may include an interface and/or functions for identifying a specific retail store and associating it with enterprise pharmacy data, including location, store configuration, and similar parameters. Store identifier 222 may enable the use of both pharmacy specific data and enterprise data and analytics, such as enterprise data store 170 and/or analytics data store 180, for assisting in an automated and/or user assisted schedule generation workflow. Pharmacy-specific data may be tracked, e.g., recorded and stored, by enterprise systems, and can include, but are not limited to, a number of register transactions per hour, a number of new prescriptions dispensed per hour, a number of refill prescriptions dispensed per hour, a percentage of new to refill prescriptions, an estimated or actual number of telephone calls per hour, a percentage of prescriptions "called-in" via a pharmacy's voice response system (voice mail), hours the pharmacy is open for business, whether the pharmacy has a drive-thru window, a maximum legal ratio of registered pharmacists to technicians required according to state law, anticipated dates and times of warehouse inventory delivery, and a predicted weekly prescription volume.

Chainwide pharmacy data, such as data for similar store configurations, locations, etc., may also be accessed from enterprise data store 170 and analytics data store 180 based on store identifier 222. Chainwide data may include data averages estimated from a multiple of pharmacies, e.g., within a specific geographical region. Chainwide data can include, but are not limited to, the timing of incoming telephone calls, the timing of voice response system "call-ins", the amount of time certain activities take, e.g., date entry, production, quality assurance, outgoing telephone calls, or cashiering transactions, rates of insurance problems, rates of refill authorization problems and frequency of customer consultation. In particular, chainwide data can help to account for staffing needs in terms of the number of staff required at each skill level and the number of man-hours required for recognition and resolution of any problems that can arise during the early stages of prescription processing, such as, prescription drop-off and data entry stages.

Operation window manager 224 may include an interface and/or functions for identifying a scheduling period and how the scheduling period should be broken into shifts and rotations to assure coverage levels during different operating periods. For example, operation window manager 224 may define two-hour operation windows and identify staffing needs across each two hour increment when configuring shifts. The volume and the timing of pharmacy activities may be predicted from the pharmacy-specific and chainwide data for a specific period of time, e.g., one week, two weeks or a month. Pharmacy activities that can be predicted with respect to volume and timing include, but are not limited to, data entry activities, such as prescription drop-off, prescription data intake, insurance adjudication review and contacting customers concerning problem resolution; production and quality assurance activities, such as dispensing drugs according to prescriptions, DUR review and customer consultation; cashiering activities; activities to handle incoming and outgoing telephone calls and faxes, e.g., to and from prescriber/doctor offices or insurance carrier offices; warehouse inventory delivery activities, meal breaks; and other downtime activities. The chainwide data may provide average times for certain pharmacy activities and can serve as relative predictors of how much time each pharmacy function or activity will take. The chainwide data predictors may be related to the store-specific volumes of the pharmacy activities, e.g., corresponding pharmacy activities, and then scaled to determine the total number of hours required for the pharmacy activities. Operations window manager 224 may predict in terms of a number or volume per hour of each day and per day of each week, such that each hour of operation of a pharmacy's business day is predicted with respect to a particular pharmacy activity. For example, the number of prescriptions dropped-off for data intake can be predicted for each hour and for each day of the time period to be scheduled.

Employee ratio selector 226 may include an interface and/or functions for selecting employee ratios of different skill levels or credentials to assure coverage during the different operating periods determined by operation window manager 224. For example, once the timing and the volume of pharmacy activities are predicted, the activities may be quantified and the total number of hours predicted. The activities may be further qualified or divided by requisite skill level, e.g., pharmacist, technician or support staff, to generate a recommended minimum number of persons required at each skill level and a recommended total number of persons required to be scheduled for a period of time including a specific hour of a day and a specific day of the week, in order to handle the pharmacy workload for that time period. Employee ratio selector 225 may convert a predicted activity into a minimum number of personnel to complete the activity in terms of the activity's requisite skill level. For instance, predicted activities include activities that can be handled only by a pharmacist, activities that can be handled either by a pharmacist, or certified or otherwise trained technician, and activities that can be handled by any staff person, including support staff. Employee ratio selector 226 may be configured to recognize those activities that can be handled by either a pharmacist or a technician, and those activities that can be handled by any staff person. For example, for the pharmacist-only activity of quality assurance, employee ratio selector 226 may predict a minimum number of pharmacists that will be required for each hour of a day and for each day of a week based upon the predicted timing and volume of pharmacist activities, including drug dispensing, customer consultation, incoming doctor calls (according to most state laws/regulations) and based upon the legal ratio of pharmacists to technicians required. The predicted minimum number of pharmacists may serve as a recommendation to the scheduler for creating a daily and a weekly staffing schedule and/or may automatically generate the pharmacist staffing value for the employee ratio (subject to minimum staffing requirements under pharmacy regulations). As another example, for activities requiring either a pharmacist or technician, such as production, employee ratio selector 226 may predict a minimum number of pharmacists plus technicians required for each hour of a day and for each day of a week. As a further example, activities that can be completed by any staff person, e.g., cashiering, would be similarly predicted as a minimum number of total staff required for each hour.

Configuration selector 228 may include an interface and/or functions for generating at least one workstation configuration for the employee ratio selected by employee ratio selector 226. For example, configuration selector 228 may use the employee ratio and store configuration to determine a configuration of workstation assignments. Once the recommended minimum number of pharmacists and technicians and the recommended total staff are determined, configuration selector 228 may produces a recommended "skeleton" staffing schedule that represents the minimum number of pharmacists, technicians and support staff required hourly and daily for the time period to be scheduled and associates pharmacist, technician, and support staff employee types or roles with the workstations necessary to cover the functions determined by operation window manager 224 and employee ratio selector 226. In some embodiments, configuration selector 228 may use a schedule record structure that generates configuration decks comprised of responsibility cards, where each responsibility card represents a set of workstation assignments and/or off-workstation tasks for each staff person. For example, a configuration deck for an employee ratio of 2 pharmacists and 3 technicians, with a total staff of 5, may include five responsibility cards, 2 for pharmacists and 3 for technicians, assigning them to specific primary and secondary workstations (or more). In some embodiments, configuration selector 228 may generate a set of configuration decks representing all viable or possible staffing configurations of workstation responsibilities at the employee ratio. The set of configuration decks may be provided in a priority order and the user may be able to navigate the set of options to select their preferred configuration of responsibilities. In some embodiments, one or more alternate configuration decks may be stored as contingent assignment records 280 for the same period.

Configuration selector 228 may generate a model schedule that identifies the number of persons required at each skill level and the work shifts of each person, e.g., indicated as times that shifts begin and end. By using configuration deck 274 and responsibility cards 276, specific workstation assignments, rotations, and off-station tasks may also be modeled in the model schedule to guide selection of employees. Actual scheduling of one or more persons to specific shifts can be accomplished using the model schedule. In some embodiments, configuration deck records for each day, shift, and rotation may be stored in pharmacy data 270 and/or passed to assignment manager 230 for assignment of staff to each responsibility card record in the configuration deck records.

Assignment manager 230 may include an interface and/or functions for generating assignments of actual staff (by name) to the configuration of workstation assignments selected by configuration selector 228. For example, assignment manager 230 may assign a set of employees associated with store identifier 222 to generate one or more proposed schedules based on the workstation responsibility configuration selected by configuration selector 228. In some embodiments, assignment manager 230 may generate a plurality of employee assignments for review and/or modification by a user. For example, assignment manager 230 may implement an iterative process of generating employee assignments, use modification, and storage to employee assignments 278 in pharmacy data 270. In some embodiments, one or more contingent sets of employee assignments may be generated for a given time period in the schedule and stored as backup configurations in contingent assignment records 280. Employee assignments may assign a name or other unique identifier for each employee in the schedule to dates, shifts, rotations, and specific responsibility cards. Pharmacy employees may be able to adjust or modify the workstation assignments made by the workstation assignment engine and the pharmacy terminal interface may include verbiage with a configurable text box that reminds pharmacy staff that workstation assignments are recommendations that can be adjusted. Relevant regulations may also be displayed and/or may be enforced by the workstation assignment engine when pharmacy staff attempt to modify the assignment cards (current or as part of the scheduling process).

In some embodiments, a pharmacy's existing schedule can be entered or downloaded into assignment manager 230 and can include existing pharmacist and technician schedules from a previous period of time, such as a previous week or month, that include total numbers of pharmacist, technician and support staff hours scheduled. Using the data of the previous work schedule may enable assignment manager 230 to compare the proposed schedule with a previous schedule to identify scheduling gaps and to direct the scheduler to changes that are required while minimizing employee availability conflicts, as described below. Assignment manager 230 may generate and recommend a "skeleton" schedule for a given period of time, e.g., one week, with the pharmacy's prior existing schedule for a similar period of time, e.g., a previous week. Assignment manager 230 may generate a gap/surplus report from the comparison of the schedules. The gap/surplus report may indicate any discrepancies between the recommended and existing schedules in terms of extra hours or shortage of hours for each hour of specific days of a week, e.g., Sunday, Monday, Tuesday, etcetera. In addition, the gap/surplus report may indicate the minimum number of total staff required for each hour of the day, and the number of RPhs and CTs to be scheduled.

In some embodiments, assignment manager 230 can provide and display a graphical daily schedule that can be configured as a user interface to permit the scheduler to make adjustments to the schedule. Each day of a week may be displayed, and within each displayed day, each hour of pharmacy operation can be displayed. Assignment manager 230 may calculate and identify any discrepancy between hours scheduled and hours needed in terms of technician hours because technician hours can be increased, decreased and shifted throughout the daily schedule without disrupting pharmacist schedules and to meet the skill level requirements identified for a specific hour of the day. The technician schedules may thereby be varied from day to day and from week to week, depending on the minimum recommended number of total staff to be scheduled per hour and the skill level required at each hour to handle the predicted pharmacy activities that occur during that hour. In some embodiments, assignment manager 230 may schedule technician hours according to the predicted timing and volume of pharmacy activities during a given hour of a given day using the workstation configuration from configuration selector 228. Assignment manager 230 may allow the scheduler to adjust a daily, weekly or monthly schedule by the hour to ensure that during each hour the pharmacy is operating, the minimum total number of staff required are scheduled and the minimum number of staff required at each skill level are scheduled.

In some embodiments, the scheduler can use assignment manager 230 and the responsibility cards and configuration decks from configuration selector 228 to assign staff of each skill level to specific workstations at specific hours of the day and during specific days of the week. The configuration decks will indicate, for instance, that on Sunday between the hours of 8:00 to 10:00 a.m., configuration selector 228 determined that one pharmacist and two technicians are required for a minimum total staff of three persons. Configuration decks 274 may be configured to indicate specific periods of time that are scheduled, e.g., from 8:00 to 10:00 a.m., 10:00 to 12 noon or 12 noon to 3:00 p.m., the minimum number of RPhs and corresponding staff persons scheduled for each time period, and the name of the person scheduled and his/her workstation assignment(s). As described below, configuration decks 274 may be used to populate work assignment interface 260 and assignment overlay 262 such that staff persons can know which workstation they are assigned to during specific hours of the day and when they need to change workstations. For example, the 3 persons scheduled to work on Sunday between 8:00 and 10:00 a.m. can thereby be assigned to one or more workstations dedicated for drop-off, production, quality assurance and pickup. During other time periods, such as between 10:00 a.m. and 12 noon and 12 noon and 3:00 p.m., additional staff can be added and/or workstation assignments can be added or changed to ensure sufficient staff having the requisite skill levels staff each workstation in response to the timing and volume of pharmacy activities. Each pharmacist and each technician can thereby be assigned to more than one workstation to help each workstation meet its tasks and to provide an overlap of staff when needed. In some embodiments, employee assignments 278 may be structured as a table, file, database, or similar data structure for associating each responsibility card 276 in each configuration deck 274 (per day, shift, rotation, etc.) with a unique employee identifier (employee name or employee ID) for the assigned employee. A similar structure of configuration decks and responsibility cards, with or without assigned employees may be used to store one or more contingent assignment records 280. For example, for each shift or rotation, one or more contingent configuration decks may be stored based on reduced staffing levels, such as one or more technicians being unavailable or a pharmacist being unavailable. In some embodiments, based on job code data being fed to the workstation assignment engine from scheduling and clock-in applications, any pharmacist punch data may be ignored and pharmacist job code will automatically populate those colleagues onto the pharmacist workstations.

Off-station task manager 232 may include an interface and/or functions for organizing and adding off-station tasks to the configuration of workstation assignments selected by configuration selector 228 and/or the employee schedule generated by assignment manager 230. For example, off-station task manager 232 may be used to assign additional tasks for specific individuals during specific times of the day. Off-station tasks may include additional pharmacy work tasks that may not be completed at a designated workstation or part of the prescription fulfillment workflow, such as restocking, inventory, receiving deliveries, equipment maintenance, cleaning, etc. These off-station tasks may still be organized and managed as part of the staffing configurations to assure that these tasks can be completed when appropriate and without undermining the workstation staffing. In some embodiments, off-station task manager 232 may enable the addition, modification, and storage of off-station tasks, as well as their assignment to off-station task responsibility cards in responsibility cards 276. These off-station task responsibility may include one or more off-station tasks that may be associated with a specific timeslot or operation window, such as a rotation, and may be included as additional "workstations" in one or more configuration decks selected by configuration selector 228. Similarly, off-station tasks responsibility cards may be assigned to specific employees by assignment manager 230 and stored in employee assignments 278.

In some embodiments, pharmacy scheduler 220 may be configured to automated operation based on scheduling selection logic embodied in rules and provided by a scheduling service in the workstation assignment engine. Pharmacy scheduler 220 may identify the pharmacy and relevant data pools using store identifier 222, generate a model of operating windows and corresponding staffing requirements using operation window manager 224, identify the appropriate employee ratio using employee ratio selector 226, determine the set of possible configuration decks for each operating window using configuration selector 228, and assign individual employees and off-station tasks using assignment manager 230 and off-station task manager 232. Pharmacists or another user tasked with scheduling or management of pharmacy tasks may be enabled to modify and rearrange the card assignment decks generated by pharmacy scheduler 220, such as adding off-station activities, modifying break times, and adding/removing an employee, which may also trigger the workstation assignment engine to recalculate the card assignments based on the new pool of eligible staff. In response to any changes to the card assignments at the pharmacy terminal, those changes may be sent to the workstation assignment engine, the workstation assignment engine may recalculate the card assignments based on the changes, and then the updated card assignments may be sent to the relevant pharmacy terminals as a new set of current assignment cards.

Pharmacists or other users may setup templates of configuration decks at the store level that incorporate ongoing regular activities, such as recurring off-station activities and meal times during the specific time intervals and at specific workstations. These customized templates may be used by the workstation assignment engine to automatically generate assignment cards and/or may allow the user at the pharmacy terminal to easily replace cards through the modification process described above. The workstation assignment engine may allow lunch breaks and other breaks to be manually and systematically assigned, updated, and incorporated into the determination of card assignments. A training engine in the workstation assignment engine may also track and analyze assignment and rotation history of individual employees to ensure staff are being developed and rotated through each workstation. The training engine may provide use this information in generating initial card assignments, as well as providing feedback to schedulers on schedule setup and modification.

Point of sale (POS) terminal 240 may include an interface protocol or set of functions, parameters, and data structures for supporting retail activities for a pharmacy, including sales transactions, return transactions, inventory search and management, etc. POS terminal 240 may also include employee authentication and functions related to staffing and timesheets. For example, POS terminal 240 may include a menu of interfaces or operations related to employee functions and these employee functions may support one or more operations of a workstation assignment engine. In some embodiments, POS terminal 240 may include a plurality of hardware and/or software modules configured to use processor 202 and memory 204 to handle or manage defined operations of POS terminal 240 for supporting real-time workstation assignments, among other POS functions. For example, POS terminal 240 may include a clock-in/clock-out interface 242 for an electronic timesheet service and a backup support request interface 244 for requesting backup support. In some embodiments, these may be pre-existing functions and interfaces of POS terminal 240 that may be configured to send notifications or otherwise trigger actions by the workstation assignment engine. In addition, POS terminal 240 may be configured as a workstation and host workstation assignment interface 260, as described below. In some embodiments, POS terminal 240 may be configured with a hot-key for initiating work assignment interface 260 and, more specifically, assignment overlay 262 to display the current workstation cards and/or configuration deck. POS terminal 240 may be configured to automatically popup assignment overlay 262 whenever there is a staffing change, rotation, or other alert or notification event.

Clock-in/clock-out interface 242 may include an interface and/or functions for enabling employees to identify to a timesheet system when they have started their shift and ended their shift. For example, an employee may log into POS terminal 240 upon arriving for their shift and open up clock-in/clock out interface 242 to log the start time of their shift for attendance and payroll purposes. Similarly, at the end of the employee's shift, clock-in/clock-out interface 242 may enable them to log the end time of their shift for attendance and payroll purposes. Clock-in/clock-out interface 242 may be configured to track employee arrivals and employee departures for determining available employees to staff a current schedule and/or assignment changes. In some embodiments, clock-in/clock-out interface 242 may also be used to track breaks for hourly employees. Clock-in/clock-out interface 242 may generate one or more messages to an enterprise timesheet service that logs employee time for use by payroll and other services. In some embodiments, clock-in/clock-out interface 242 and/or the timesheet service receiving the work start and work stop times from clock-in/clock-out interface 242 may generate a message to the workstation assignment engine and, more specifically, a staffing change service that tracks the employees present and working in the pharmacy at any given time. POS terminal 240 may automatically send clock-in and clock-out information to the workstation assignment engine for each clock-in or clock-out event for each employee. Responsive to each employee arrival and/or departure, the staffing change service may be configured to evaluate the current staff against the prior staffing configuration and/or the scheduled staffing configuration to determine whether the current configuration is fully supported by the staff present, or a new configuration of assignments needs to be generated based on the staffing change and any gaps or excess in the staff present. In some embodiments, other subsystems for tracking employee presence may be used, such as automated and/or security-based tracking of employees on premises, to determine the availability of employees for staffing assignments.

Backup support request interface 244 may include an interface and/or functions for allowing active staff to request additional staff support for one or more POS terminals, workstations, and/or off-station tasks. For example, POS terminals at pickup, drop-off, and/or drive-thru workstations may be used to indicate when a number of waiting customers has exceeded a desired queue depth and request backup at one or more customer-facing positions. Similarly, arrival of a delivery, escalation of a customer service issue, emergencies, temporary loss of a staff member, and/or similar situations that may require immediate reshuffling of responsibilities of the remaining staff may be identified through backup support request interface 244. In some embodiments, backup support request interface 244 may include a graphical user interface for selecting the type of backup requested and/or the situation requiring a change in staffing assignments. In some embodiments, backup support request interface 244 and/or a notification service receiving the backup request from backup support request interface 244 may generate a message to the workstation assignment engine and, more specifically, a staffing change service that tracks the employees present and working in the pharmacy at any given time. Responsive to a backup request and/or the change in staffing, workstation, and/or off-station tasks the backup request contains or requires, the staffing change service may be configured to evaluate the current staff against the prior staffing configuration and/or the scheduled staffing configuration to determine whether a new configuration of assignments can be generated to support the backup request. When backup support is requested at POS terminal 240, the backup notification may be sent to the workstation assignment engine and the workstation assignment engine may send the notification to other pharmacy terminals with the corresponding backup colleague's name, workstation assignment, and/or other messages as appropriate. In some embodiments, the backup notification may generate an indication of reassignment to one or more staff through work assignment interface 260. In some embodiments, responsive to the backup request, each workstation display may populate a notification window within the workstation display with a backup request message.

Pharmacy workflow manager 250 may include an interface protocol or set of functions, parameters, and data structures for supporting prescription fulfillment activities for a pharmacy, including prescription intake, data entry, production, quality assurance, pickup, etc. For example, each workstation may be configured with pharmacy workflow manager 250 as an application that interacts with an enterprise workflow system and one or more enterprise data stores (such as patient records, prescription records, pharmaceutical databases, insurance records, etc.) to organize and manage the various steps in the prescription fulfillment process. In some embodiments, pharmacy workflow manager 250 may include a plurality of hardware and/or software modules configured to use processor 202 and memory 204 to handle or manage defined operations of pharmacy workflow manager 250. For example, pharmacy workflow manager 250 may include a workstation task manager 252 for displaying and supporting workstation tasks and a task queue 254 for displaying and managing the queue of tasks to be completed at each workstation for prescriptions in progress. In some embodiments, these may be pre-existing functions and interfaces of pharmacy workflow manager 250 and may provide the existing graphical user interfaces over which host workstation assignment interface 260 may be displayed, as described below.

Workstation task manager 252 may include an interface and/or functions for allowing the staff at a workstation computing system to use that workstation computing system to complete one or more tasks for processing a prescription in accordance with the role of that workstation and staff. For example, workstation task manager 252 may include a plurality of graphical user interfaces, menus (or other navigation options), and guided workflows for entering and retrieving information related to their task, as well as controlling peripheral devices, such as bar code readers, label printers, scales/counters/sorters, and other devices for completing their tasks. Workstation task manager 252 may populate the graphical user interface of a workstation computing device with information specifically related to executing the assigned workstation tasks.

Task queue 254 may include an interface and/or functions for allowing staff at a workstation computing system to identify and select prescription processing tasks to complete that are relevant to the workstation assignment. For example, each workstation may include a task queue that indicates pending prescriptions to be processed, where they are in the workflow process, and what specific tasks are available for advancing processing of the pending prescriptions. Task queue 254 may display a graphical user interface to the workstation user that indicates the current task being worked on by the workstation user and the queue of waiting additional tasks that may be processed by the workstation user. Note that in some configurations, there may be multiple workstations of the same time and those workstations may be configured to work from a common queue and/or an enterprise workflow system may specifically allocate tasks between multiple workstations of the same type. In some embodiments, task queue 254 may include a queue depth that equals the number of pending and/or unstarted tasks in task queue 254 and this queue depth may be used as an indicator of the need for additional allocation of staff to the same workstation type (high queue depth) or an indicator of the availability of staff to be allocated to a different workstation or off-station task.

Work assignment interface 260 may include an interface protocol or set of functions, parameters, and data structures for displaying, navigating, and/or overriding workstation assignments generated by a workstation assignment engine. For example, each workstation, regardless of whether it is configured as a pharmacy workflow workstation hosting pharmacy workstation task manager 252 and/or a POS terminal 240, may be configured to display work assignment interface 260 to coordinate staff visibility into current staffing assignments, scheduled staffing assignments, and any changes in staffing configuration that are responsive to staffing change events. Work assignment interface 260 may be enabled on all workstation terminals or pharmacy computing systems and may include a hot-key, menu, and/or other navigation options for initiating and displaying work assignment interface 260 and, more specifically, assignment overlay 262. Workstation assignment interface 260 may include a limited view, such as a popup for assignment overlay 262 that occupies a portion of the display, and an expanded view that uses substantially all of the display area or generates a new window, such as schedule viewer 264 and/or override manager 266. Work assignment interface 260 may be configured for two-way communication with the workstation assignment engine, sending and receiving modifications, workstation cards, and configuration decks on demand.

In some embodiments, work assignment interface 260 may include a plurality of hardware and/or software modules configured to use processor 202 and memory 204 to handle or manage defined operations of work assignment interface 260. For example, work assignment interface 269 may include an assignment overlay 262 for displaying current assignments and assignment changes, a schedule viewer 264 for navigating the broader schedule of work assignments, and an override manager 266 for enabling some staff to override scheduled assignments and/or system-generated assignment changes.

Assignment overlay 262 may include an interface and/or functions for displaying the current work assignments on each workstation interface. For example, assignment overlay 262 may be configured by a current assignment overlay service and published by the workstation assignment engine to each workstation for display as a popover on a portion of the graphical user interface of the workstation. Assignment overlay 262 may automatically popup in response to staffing changes, such as a change in the number or ratio of employees working, rotations, and/or other notification or alert conditions. In some embodiments, assignment overlay 262 may be provided as a graphics file, markup file (e.g. hypertext markup language (HTML), extensible markup language (XML), etc.), set of parameters for a graphics rendering function, etc. to each workstation computing system. In some embodiments, assignment overlay 262 may be implemented on a computer display and a related set of assignment or responsibility "cards" for an operating window may be referred to and displayed as an assignment or configuration "deck". These cards and decks may be configured for different store layouts (including drive-thru, walk-up, clinic, etc.) and workstation configurations (number of drop off, production, QA, pickup, drive thru, and other stations). In addition, different staffing levels and staffing configurations within those staffing levels may be represented by different decks as described elsewhere herein.

In some embodiments, assignment overlay 262 may include at least one workstation card 262.1 displaying the assignment or assignments and associated employee currently assigned to the workstation displaying assignment overlay 262. For example, the workstation associated with the primary workstation assignment on a responsibility card 276 may display the information from the responsibility card as a workstation card 262.1 in assignment overlay 262. Workstation card 262.1 may be defined by the workstation identifier for the workstation on which it is displayed and may be highlighted (e.g., bold text, contrasting color, preferred positioning, or other visual indicator of priority) as the responsibility information for the person who should be present at that workstation. Example workstation identifiers may include numeric codes, text descriptors, and/or name strings, such as "Production 1", "Production 2", "Drop-Off", "Pick-Up", Drive-Thru", "Quality Assurance", etc. In some embodiments, workstation card 262.1 may include an ordered list of responsibilities that indicate a primary responsibility (primary work station) and any number of additional responsibilities, such as additional workstations or other tasks. In some embodiments, workstation card 262.1 may be displayed as part of assignment overlay 262 on all workstations identified in the responsibility list. In some embodiments, each workstation interface may display as many different workstation cards as there are responsibility cards 276 for the current configuration of assignments in configuration deck 262.2. Configuration deck 262.2 may include all responsibility cards 276 for the current employee assignments embodied for display as workstation cards 262.1 Depending on the number of responsibility cards and available interface area, all workstation cards 262.1 may be displayed at once in assignment overlay 262 and/or assignment overlay 262 may enable scrolling or some other means of navigating through configuration deck 262.2.

In some embodiments, assignment overlay 262 may include window parameters indicating the operating window in which the current assignments are scheduled or active. For example, assignment overlay 262 may include a text graphical element that indicates a start time and stop time for the current assignments and may indicate whether a rotation, shift change, store open, store close, temporary change, override, or similar condition governs the beginning and/or end of the operating window.

In some embodiments, assignment overlay 262 may include notification parameters 262.4 indicating schedules changes, unscheduled change notifications, and other notification to the user to support assignment notifications and changes. For example, assignment overlay 262 may include a message area and/or status value (text, icon, color bar, etc.) that communicates whether a current, pending, or potential change necessitates attention from the user. In some embodiments, assignment overlay 262 may disappear during normal operation of the workstation computing system for its workstation or POS functions and may appear as a popover responsive to notification parameters 262.4. Where assignment overlay 262 appears as a temporary reconfiguration of the user interface (e.g., popover, popup, window, etc.) in response to a notification condition, assignment overlay 262 may also be available on demand through a menu, icon, hot-key, or some other navigation option from the primary workstation or POS user interface.

In some embodiments, off-station assignments 262.5 may also be included among responsibility cards 276 and assignment overlay 262 may be configured to display off-station assignments. For example, one or more off-station task cards containing off-station assignments 262.5 may be included in configuration deck 262.2 and displayed alongside workstation cards 262.1. In some embodiments, off-station assignments 262.5 may be included on workstation cards 262.1 for employees who have a combination of workstation and off-station assignments. In some embodiments, work assignment interface 260 may support publication of assignment overlay 262 to mobile devices, such as an application on a user's mobile phone or tablet, and the mobile device of the employee assigned may be treated as another workstation for the purposes of assignment overlay 262. For example, the mobile application may display workstation cards 262.1, configuration deck 262.2, window parameters 262.3, notification parameters 262.4, off-station assignments 262.5 and/or presence indicator 262.6 configured for a smaller mobile display.

In some embodiments, assignment overlay 262 may include a presence indicator 262.6 that indicates which employees are physically present. For example, each workstation card 262.1 may include an icon, color indicator, or similar feature indicating that the assigned employee is clocked-in and available for their assigned responsibility. In some embodiments, presence indicator 262.6 may further indicate which workstation and/or task each employee is engaged in on their respective workstation cards 262.1 and/or off-station assignments 262.5. For example, the workflow assignment engine may maintain a set of location indications for each employee based on log-ins to workstations, location data from mobile devices, location indications provided by the users through work assignment interface, etc. Each workstation card 262.1 may include a highlight, icon, or other indicator for the specific workstation or off-station task with which the employee was most recently engaged.

Schedule viewer 264 may include an interface and/or functions for displaying and navigating assignments for other operating windows on each workstation interface. For example, schedule viewer 264 may enable the user to selectively access a schedule view of configuration decks organized by operating windows (such as rotations). In some embodiments, initiating schedule viewer 264 may increase the graphical user interface area used by work assignment interface 260 to a larger window or full-screen mode for easier navigation of schedule information. Schedule viewer 264 may display configuration decks and their respective workstation cards on a navigable grid where rows correspond to operating windows and columns correspond to primary workstation assignments or employee. Schedule viewer 264 may enable a user at any workstation to navigate forward and/or backward in time to see past or future assignments for themselves and/or their coworkers.

Override manager 266 may include an interface and/or functions for changing assignments for current and/or future operating windows from a workstation interface (with the proper credentials). For example, a pharmacist, pharmacy manager, shift manager, or other employee with override credentials may use access override manager 266 to change the names assigned to responsibility cards 276 in real-time based on a perceived need for a configuration change. In some embodiment, override manager 266 may include a limited set of scheduling functions that enable employee assignments to be reconfigured, such as dragging and dropping or selecting from an employee drop-down, the employees assigned to each responsibility card. In some embodiments, override manager 266 may enable the user to override or use an actual staffing ration that is different from the scheduled staffing ratio to generate new configuration decks and responsibility cards. Override manager 266 may invoke pharmacy scheduler 220 and/or a more limited set of similar functions to select employee ratios, generate and select configuration deck options, and assign responsibility cards and off-station tasks. Override manager 266 may invoke a set of override rules enforced by the rules engine of the workstation assignment engine and these override rules may be in addition to the normal master, regulatory, and store preference rules enforced in pharmacy scheduler 220 and the automated assignment changes generated by staffing change service 140.

Figure 3:
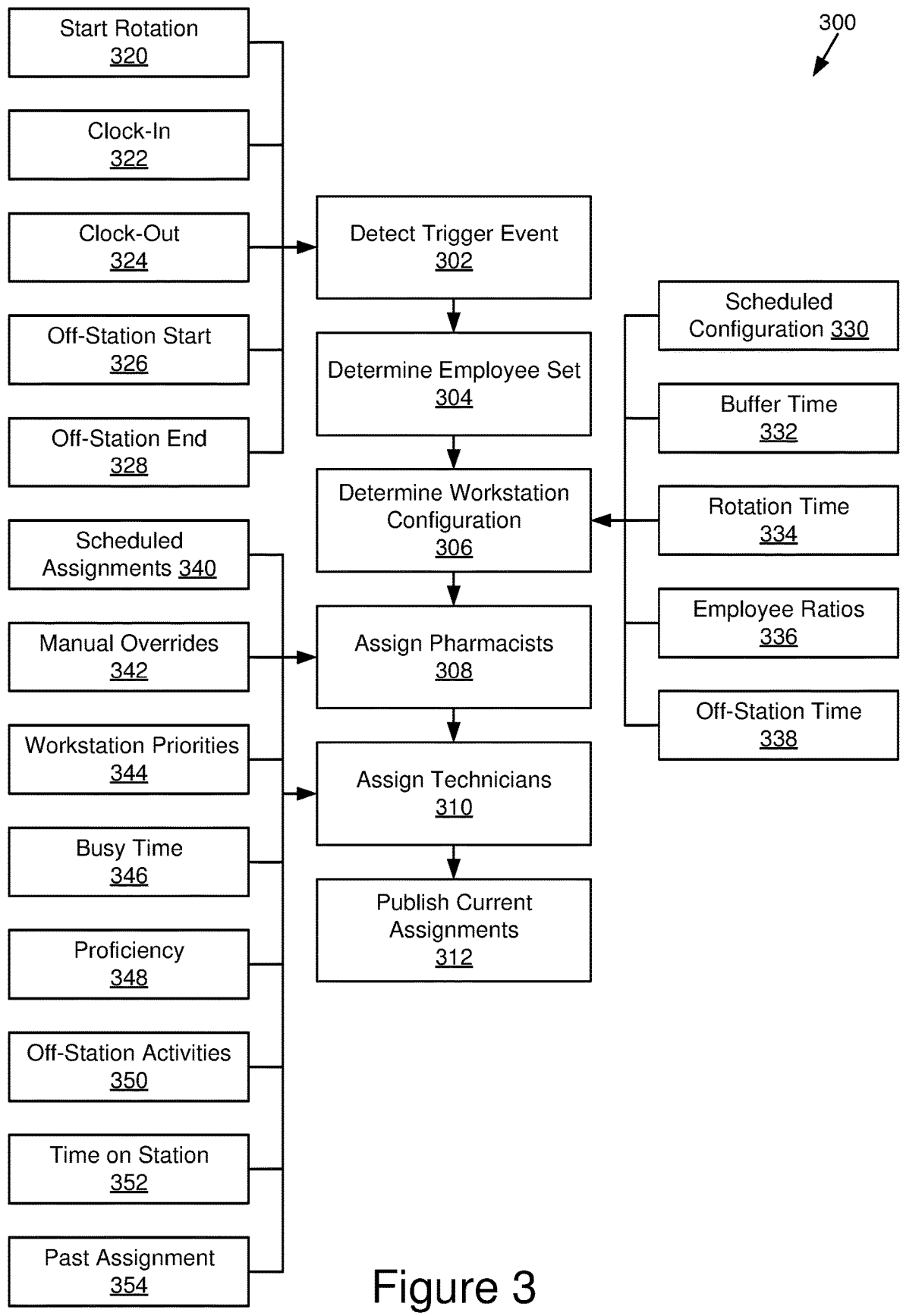
FIG. 3 is a flowchart of an example method of dynamically assigning and displaying workstation assignments.

FIG. 3 shows an example method 300 of dynamically assigning and displaying workstation assignments. For example, pharmacy information system 100 of FIG. 1 and/or pharmacy computing system(s) 200 of FIG. 2 may be operated in accordance with blocks 302-312 of method 300 to assign and display workstation assignments by evaluating parameters and rules related to blocks 320-354.

At block 302, a trigger event for determining a new set of workstation assignments may be triggered. For example, a staffing change service may monitor one or more other services for detecting staffing change events, which may include changes in the staff available and/or changes in the staffing needs.

At block 304, an employee set may be determined for the workstation assignments. For example, an assignment generator may identify a pool of available employees in a real-time reconfiguration of workstation assignments based on the set of employees that are clocked-in according to a timesheet service. As another example, the assignment generator may identify a pool of available employees in a scheduling process based on all active employees for a store, a subset selected for a particular day or shift, and/or prior schedule data for that store.

At block 306, a workstation configuration may be determined. For example, the assignment generator may evaluate a plurality of configuration decks that meet the employee ratios in the employee set, physical configuration of workstations for the particular store, and the master, regulatory, and store workstation configuration rules. The possible configuration decks that meet the rules may then be prioritized by the assignment generator to provide a selected configuration deck and one or more contingent configuration decks.

At block 308, pharmacists may be assigned to responsibility cards from the selected configuration deck. For example, the assignment generator may select from among the pharmacists in the employee set to assign responsibility cards that require pharmacist credentials.

At block 310, technicians may be assigned to responsibility cards from the selected configuration deck. For example, the assignment generator may select from among the technicians in the employee set to assign responsibility cards that do not require pharmacist credentials. In some embodiments, method 300 may be configured to manage workstation assignments and tasks across more than two levels of employee credentials or qualifications for particular workstations or tasks, such as general customer support staff or specialized clinical staff.

At block 312. current assignments may be published to all workstations. For example, a current assignment overlay generator may publish the configuration deck with employee names assigned to each responsibility card for publication as workstation cards on each workstation.

In some embodiments, a plurality of trigger events may be monitored for the detection of a trigger event at block 302. For example, the staffing change service may receive notification of one or more of these change event types and include logic (with or without the support of a rules engine) to determine whether a dynamic reconfiguration of assignments should be initiated. A start rotation event 320 may be a time-based event that follows the scheduled rotations for the day and shift and/or a default rotation period for a store or enterprise. For example, a start rotation event 320 may be detected every two hours during normal operation of a retail pharmacy, though other rotation times are possible. A clock-in event 322 or a clock-out event 322 may be detected each time an employee punches in or punches out, such as at the start and end of a shift, or for breaks or meals within a shift. An off-station start event 326 or an off-station end event 328 may be detected each time and employee starts of completes an off-station task or series of off-station tasks. For example, the employee may indicate log onto or log off an assigned workstation, select an off-site task from a task queue, or otherwise indicate to the staffing change service that he or she is engaging in an off-site task and unavailable to cover workstation tasks for some period of time.

In some embodiments, a plurality of configuration selection parameters may be considered for determining workstation configuration at block 306. For example, the assignment generator may apply a series of logical rules to parameters related to selecting a new workstation configuration. A scheduled configuration 330 may apply based on the trigger event. For example, start rotation event 320, clock-in event 322, clock-out event 324, off-station start event 326, and/or off-station end event may coincide with a scheduled rotation or shift change and a configuration deck previously configured for the operating window may apply. This may be the default and most common condition, where the configuration deck and responsibility cards selected by a pharmacy scheduler accurately reflect the staff resources and needs. A buffer time 332 may provide an additional window for the available staff resources and/or staff needs to align with schedule configuration 330. For example, buffer time 332 may include an elapsed time, such as 5 or 10 minutes, before or after a scheduled operating window and during which the scheduled configuration may be maintained to allow for staff being early or late for their shifts. Rotation time 334 may include a default rotation time, such as every two hours. In some embodiments, rotation time 334 may be applied to a shift schedule independent of the original scheduling activity. Scheduled configuration 330 may be applied to the first rotation of a shift, but the assignment generator may be called on for each rotation within the shift and may dynamically generate the rotations. Additionally, rotations may impact the assigned employees in blocks 308 and 310, but not the actual workstation configuration deck. Employee ratio 336, which may include both the ratio of pharmacists to technicians and the total staffing level, may be used by the assignment generator in the event that, after buffer time 332, a different employee ratio 336 is present than anticipated in scheduled configuration 330. For example, if one or more employees has failed to clock-in or has been assigned to an unscheduled off-station task, the scheduled configuration deck may no longer work and a contingent configuration deck will need to be selected that reflects the reduced available staffing. Off-station time 338 may reflect breaks, meals, and other activities that remove staff (generally temporarily) from the set of employees available to cover the responsibility cards in the scheduled (or a dynamically generated) configuration deck. The assignment generator may include logic for calculating, enforcing employment regulations related to, and otherwise compensating for changes in available staff due to off-station time 338.

In some embodiments, a plurality of employee assignment parameters may be considered for assigning pharmacists at block 308 and/or assigning technicians at block 310. For example, the assignment generator may apply a series of logical rules to parameters related to selecting the responsibility assignments for a new workstation configuration. As with determining the workstation configuration, scheduled assignments 340 may apply based on the trigger event. However, some systems and users may not include assignments within the schedule (scheduling only to the shift level and not for specific assignments and rotations), may schedule assignments for only a first rotation, or may generate dynamic configuration decks that no longer match scheduled assignments 340. Manual overrides 342 may include situations where a real-time decision is made by an employee with authority to override one or more aspects of scheduled assignments 340. In some cases, this may include overriding workstation configurations and/or specific employee assignments thereunder.

If scheduled assignments 340 and/or manual overrides 342 are not sufficient to determine all assignments and/or violate one or more assignment rules, additional assignment parameters may be evaluated. The assignment rules may include workstation priorities 344 that determine the order in which at least one responsibility card with a primary responsibility of the highest priority not yet assigned, must be the next assigned to available staff in the set of employees (and as appropriate for their qualifications). For example, workstation coverage may be prioritized by: 1) drop-off, 2) drive-thru, 3) pickup, 4) production for technicians (or pharmacists if quality assurance is already covered). Busy time 346 may identify operating windows, generally rotations, in which specific workstations tend to be most busy, particularly customer facing workstations like drop-off, drive-thru, and pickup. During these busy times, redundancy (e.g., assigning two or more drop-off workstations, etc.) may be allocated to busy functions, in addition to giving them priority. Proficiency 348 may be used to give preferential assignment to employees with higher proficiency ratings, particularly for high priority and/or busy time workstations. Off-station activities 350 may include a prioritization scheme for assigning off-station activities. For example, receipt of deliveries and/or other time-sensitive tasks may be given high priority, while background maintenance tasks may be given lower priority and not assigned until higher priority workstations and off-station tasks are assigned. Periodic off-station activities, such as restocking, cleaning, ordering, etc., may have a low priority after completion that increases as time passes and the activity becomes critical and/or approaches a specific deadline (such as an ordering deadline for a weekly shipment). Time on station 352 may monitor how long each employee has worked at a particular workstation to make sure workstations are rotated in a reasonable manner. For example, best practices, health and safety, or other regulations may set maximum times that an employee may work at a particular type of station and/or the same station. Employees that have met their maximum time on station need to be rotated to a different assignment and proactive rotation of employees before they have reached their maximum may be implemented to preserve flexibility for later rotations, overlapping shifts, and/or busy times. Similar to time on station, past assignments 354 may be used to determine new assignments. There is a switching cost to having employees change stations in terms of wind down of a current assignment and setup of a new assignment. So, if other rules do not recommend changing an assignment, the assignment generator may give preference to keeping employees at their current workstations.

Figure 4:
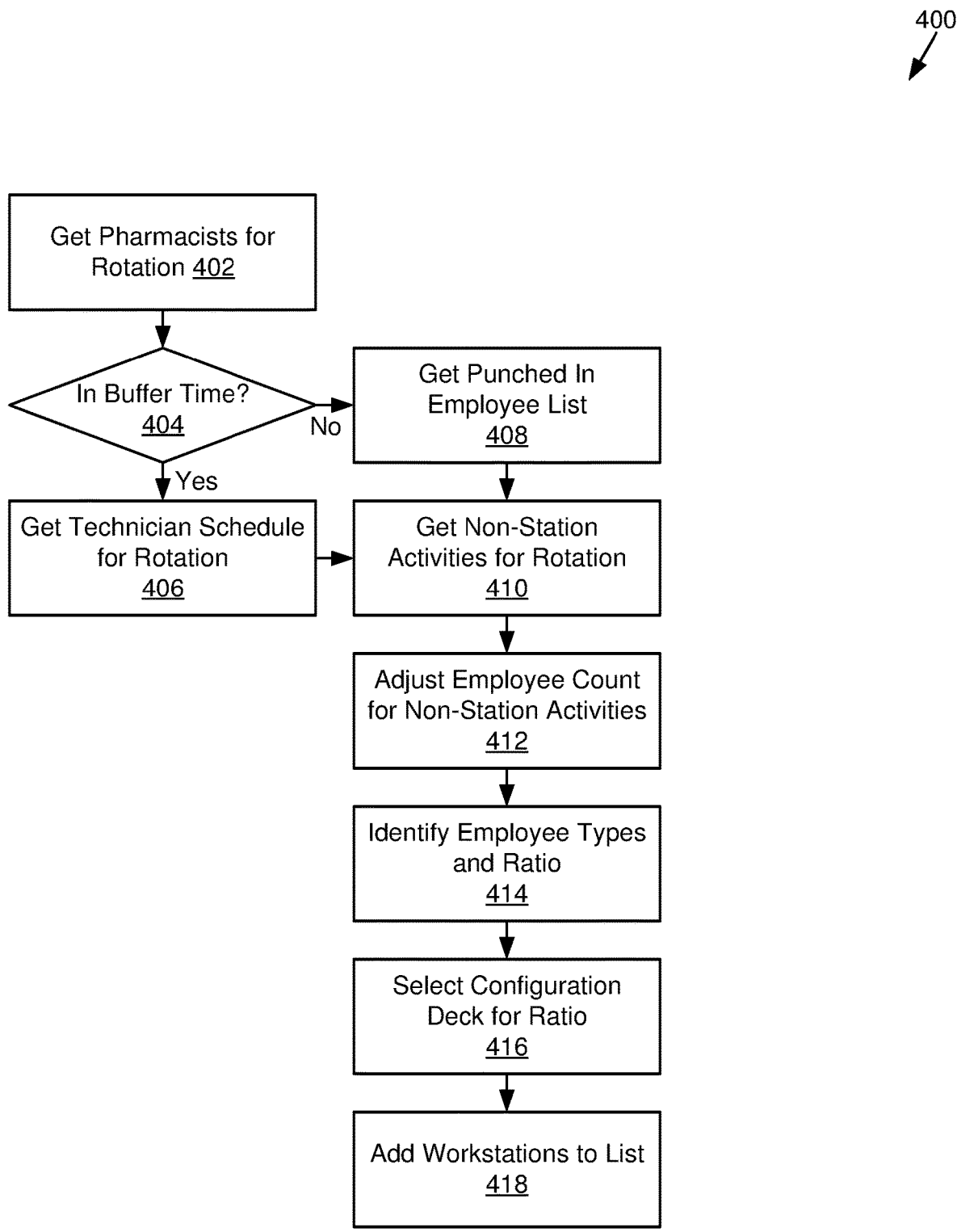
FIG. 4 is a flowchart of an example method of dynamically determining a workstation configuration.

FIG. 4 shows an example method 400 of dynamically determining a workstation configuration. For example, pharmacy information system 100 of FIG. 1 and/or pharmacy computing system(s) 200 of FIG. 2 may be operated in accordance with blocks 402-418 of method 400 to determine the workstation responsibility cards for a configuration deck.

At block 402, the pharmacists for a rotation may be gotten. For example, an assignment generator may determine the pharmacists for the rotation from a schedule record for the day and shift.

At block 404, whether or not the assignment process is within buffer time may be determined. If yes, buffer time is still available for employees to punch in and method 400 may proceed to block 406. If no, buffer time has expired and method 400 may proceed to block 408.

At block 406, the technician schedule for the rotation may be gotten. For example, the assignment generator may determine the scheduled technicians from the schedule record for the day and shift.

At block 408, a punched employee list may be gotten. For example, the assignment generator may determine the punched in employees from a timesheet service.

At block 410, non-station activities may be gotten for the rotation. For example, a list of off-station activities and their priority may read from the schedule record and/or an off-station task list and assembled into one or more responsibility cards for off-station tasks (depending on the number and type of employees necessary to complete the high priority off-station tasks during the rotation).

At block 412, the employee count may be adjusted for non-station activities. For example, employee types and counts assigned to off-station tasks are no longer available in the set of employees for allocating workstation responsibilities.

At block 414, the employee types and employee ratio may be identified. For example, the assignment generator may determine an updated employee ratio (based on employee types) and staff count based on the reduction in available workstation staff at block 412. For example, the actual employee ratio may be one pharmacist to four technicians (1:4), but one of the technicians may need to be assigned to non-station activities, leaving a ratio of 1:3.

At block 416, a configuration deck may be selected for the employee ratio. For example, the assignment generator may evaluate all possible configuration decks for the store configuration based on the employee ratio, prioritize the possible configuration decks based on configuration parameters, and select the highest priority configuration deck for the employee ratio.

At block 418, the workstations are added to a list of responsibilities for assignment to employees. For example, the configuration deck may include a plurality of responsibility cards organized by their primary workstation responsibility (though each responsibility card may include one or more secondary workstation responsibilities as well) and these responsibility cards may be translated into a list of workstation cards for use in assigning employees.

Figure 5:
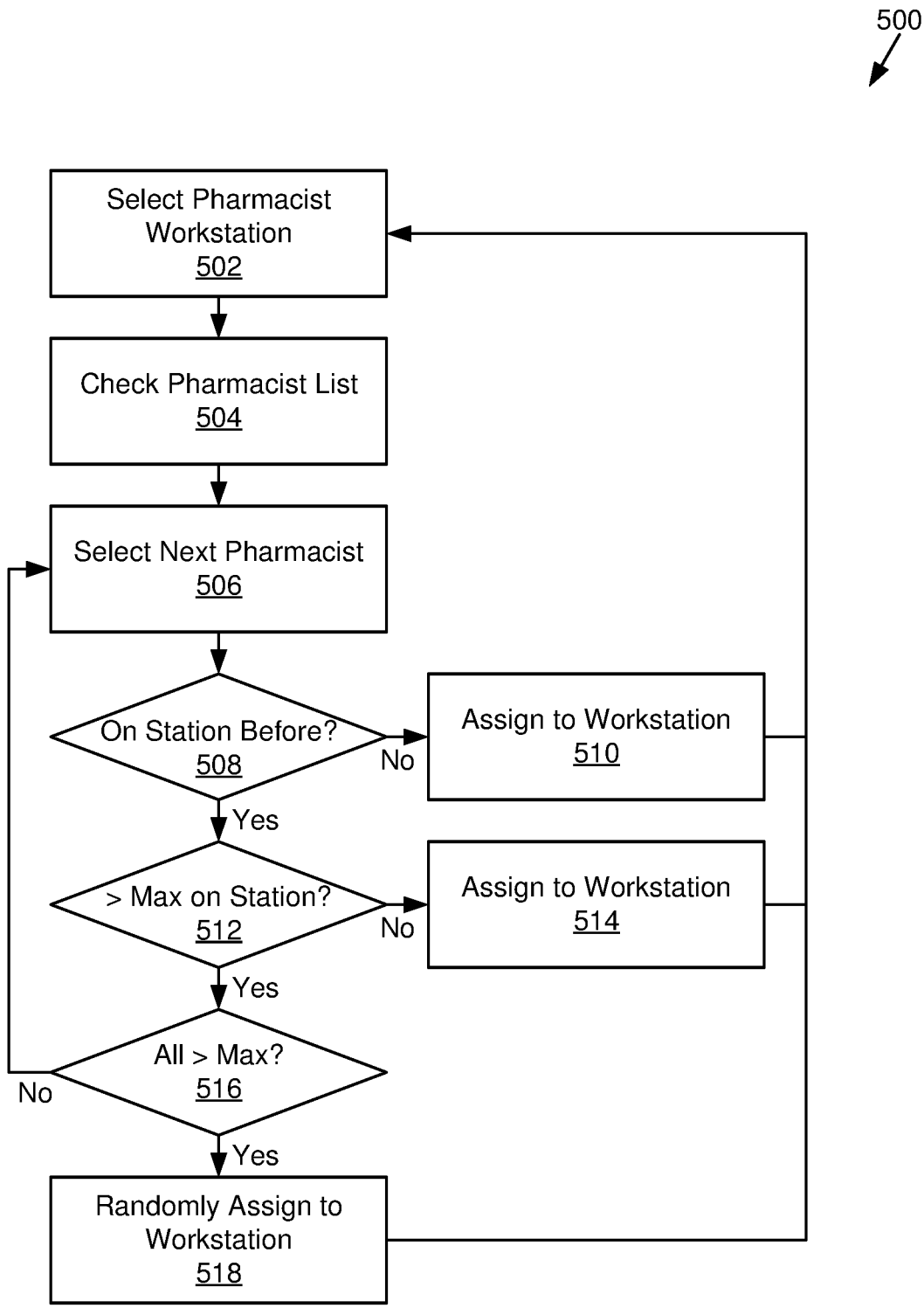
FIG. 5 is a flowchart of an example method of dynamically assigning pharmacists to workstations.

FIG. 5 shows an example method 500 of dynamically assigning pharmacists to workstations. For example, pharmacy information system 100 of FIG. 1 and/or pharmacy computing system(s) 200 of FIG. 2 may be operated in accordance with blocks 502-518 of method 500 to assign the workstation responsibility cards for a configuration deck to the available pharmacists.

At block 502, a pharmacist workstation may be selected. For example, the assignment generator may select a responsibility card that requires pharmacist credentials if there are any remaining pharmacist responsibility cards in the configuration deck.

At block 504, a pharmacist list may be checked. For example, the assignment generator may check the available pharmacists in the schedule record for the day and shift.

At block 506, the next pharmacist may be selected. For example, the assignment generator may select the next pharmacists from the list of available pharmacists in the schedule record.

At block 508, whether the pharmacist has been on this workstation before may be evaluated. If no, method 500 may proceed to block 510 and assign the selected pharmacist to the workstation. If yes, method 500 may proceed to block 512.

At block 512, whether the pharmacist has exceeded the maximum time on the selected workstation may be determined. If no, method 500 may proceed to block 514 and assign the selected pharmacist to the workstation. If yes, method 500 may proceed to block 516.

At block 516, whether all of the pharmacists have exceeded the maximum time on the selected workstation may be determined. If no, method 500 may return to block 506 and select the next pharmacist to evaluate for assignment to the workstation. If yes, method 500 may proceed to block 518.

At block 518, an unassigned pharmacist from the pharmacist list may be randomly assigned to the selected workstation. For example, the assignment generator may randomize among the unassigned pharmacists on the list and associate the randomly selected pharmacist's name and/or employee ID with the workstation card and/or associated responsibility card.

Figure 6:
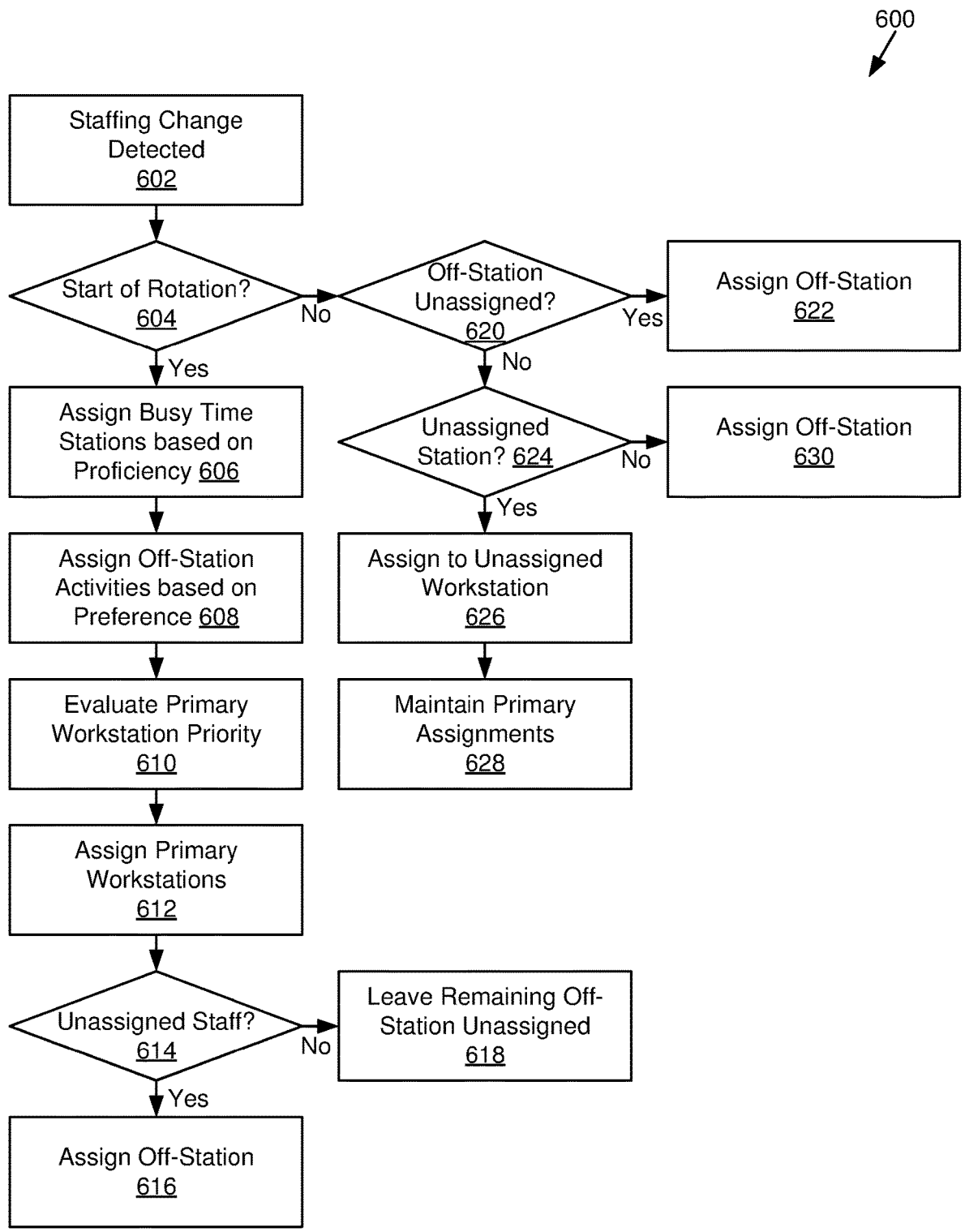
FIG. 6 is a flowchart of an example method of dynamically assigning technicians to workstations.

FIG. 6 shows an example method 600 of dynamically assigning technicians to workstations and off-station tasks. For example, pharmacy information system 100 of FIG. 1 and/or pharmacy computing system(s) 200 of FIG. 2 may be operated in accordance with blocks 602-630 of method 600 to assign the workstation responsibility cards for a configuration deck to the available technicians.

At block 602, a staffing change may be detected. For example, a staffing change service may detect a change in staffing.

At block 604, whether it is the start of a rotation may be determined. If yes, method 600 may proceed to block 606. If no, method 600 may proceed to block 620.

At block 606, busy time stations may be assigned based on proficiency. For example, assignment generator may identify primary workstations subject to busy time indications and select a technician to assign based on the highest available proficiency at that workstation.

At block 608, off-station activities may be assigned based on preference. For example, the assignment generator may select off station activities and/or an off-station responsibility card and assign it to a technician that has a preference for off-station tasks and/or one or more off-station activities specifically identified.

At block 610, primary workstation priority may be evaluated. For example, the assignment generator may evaluate the priority of remaining workstation cards and organize them in priority order for assignment.

At block 612, primary workstations may be assigned in priority order. For example, the assignment generator may select an employee to assign to each remaining workstation based on proficiency at the selected workstation and/or random assignment.

At block 614, whether there are unassigned staff remaining may be determined. If yes, method 600 may proceed to block 616. If no, method 600 may proceed to block 618.

At block 616, off-station tasks may be assigned to the unassigned staff. For example, the assignment generator may assign the remaining staff to lower priority off-station tasks that were not assigned at block 608.

At block 618, remaining off-station tasks may remain unassigned. For example, the assignment generator may not have any remaining staff to cover lower priority off-station tasks and may leave those off-station tasks in a task queue for re-evaluation during a later staffing change.

At block 620, whether off-station tasks remain unassigned may be determined. If yes, method 600 may proceed to 622. If no, method 600 may proceed to block 624.

At block 622, the off-station tasks may be assigned. For example, the assignment generator may assign unassigned tasks to an off-station responsibility card and associate an available technician with the off-station responsibility card.

At block 624, whether there is an unassigned station based on a change is staffing ratio may be determined. If yes, method 600 may proceed to block 626. If no, method 600 may proceed to block 626.

At block 626, an unassigned technician may be assigned to the unassigned workstation. For example, the assignment generator may identify an unassigned workstation based on the staffing change and assign it to an unassigned technician, if available.

At block 628, primary assignments may be maintained by the assignment at block 626. For example, the assignment generator may maintain primary workstation assignments generated at block 612 by assigning the unassigned workstation to assure primary workstation coverage.

At block 630, an unassigned technician may be assigned to off-station tasks. For example, the assignment generator may assign the unassigned technician to any remaining off-station tasks that have not been previously assigned, which may include lower priority off-station activities.

Figure 7A:
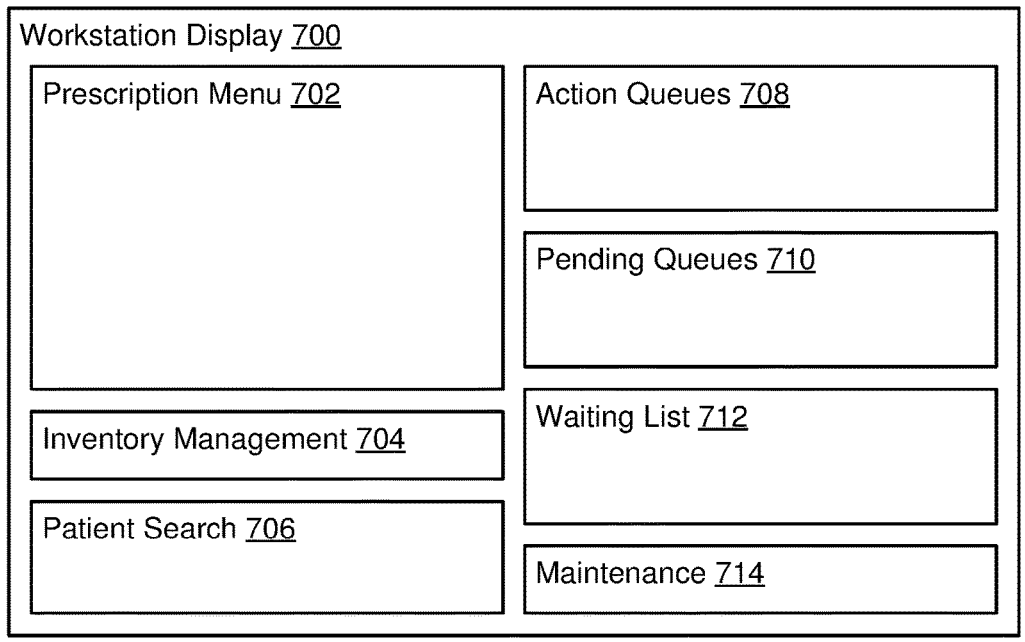
FIGS. 7a and 7b are block diagrams of an example workstation interface configured to display workstation assignments.
Figure 7B:
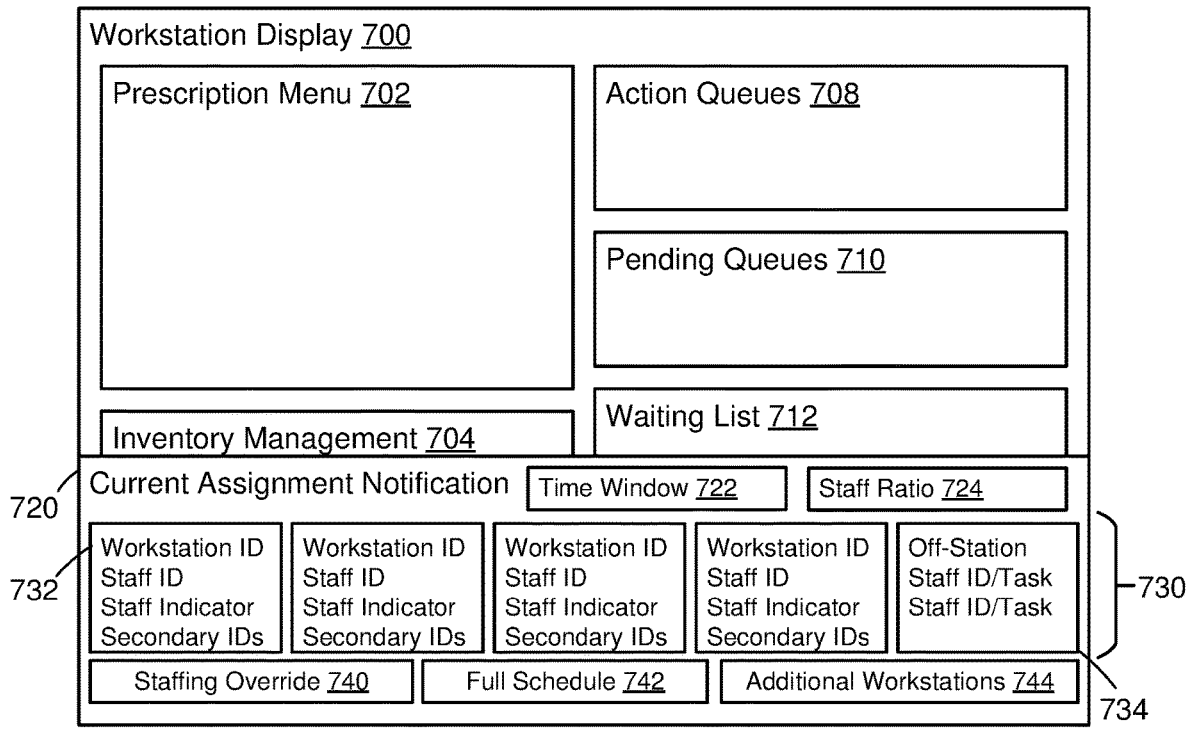

FIGS. 7a and 7b show an example graphical user interface for a pharmacy workstation terminal, such as a pharmacy computing system 104 in FIG. 1 or pharmacy computing system 200 in FIG. 2. Workstation display 700 may define some or all of a display area, such as monitor or a window displayed on a monitor, configured for using one or more workstation applications.

FIG. 7a may show workstation display 700 during normal operating mode for the workstation, such as providing workflow support for one or more prescription fulfilment tasks. For example, prescription menu 702 may support functions like batch refill, prescription transfer, edit prescription, generate new prescription, label reprint, calculate price, check fill status, inactivate refills, batch return to stock, formulary check, and delete prescription. Inventory management 704 may initiate an inventor management interface for searching and managing inventory. Patient search 706 may enable both local and global searches for patient records. Action queues 708 may include the waiting queues for different workstation types, such as production, verification, and drive-thru, as well as special handling queues, such as triage and request calls, reflecting actions that can be taken by available staff. Pending queues 710 may include other queue types, such as downtime, exceptions, inventory, requests, and patient care. Waiting list 712 may include a list of patients waiting for prescription fulfilment or other actions, generally on-site. Maintenance 714 may include interfaces for other functions to support operation of the workstation and pharmacy workflow, such as access to reports, system functions, patient care action items, batch printing, and prescriber, insurance, and help desk contacts.

FIG. 7b may show workstation display 700 with a current assignment overlay covering a bottom portion of workstation display 700. For example, current assignment notification 720 is a horizontal workstation assignment notification spanning the width of the screen and covering less than half of workstation display 700. In some embodiments, current assignment notification 720 may automatically popup from the bottom of the screen, display for X seconds (where X is a configurable value), then disappear. In other embodiments, current assignment notification 720 may be displayed until dismissed and may include a close icon (such as an X in the upper right corner) for this purpose. Other popup or popover configurations are possible, such as side, top, center, or other locations with different dimensions, shapes, aspect ratios, etc. Current assignment notification 720 may appear any time there is a change to the staffing (punch in/out), at the start of a designated off station task, at the start of a new rotation period (i.e. 8 am-10 am, 10 am-noon, noon-2 pm), or based on another alert or notification, such as a backup request. Note that the rotation period may be a configurable value.

Current assignment notification 720 may include an operating or time window 722 and a staff ratio 724 to clearly communicate the current staffing parameters. For example, time window 722 may provide the start and stop time for the current rotation or shift and staff ratio 724 may include the number of pharmacists and technicians currently clocked in.

Current assignment notification 720 may include graphical display of a configuration deck 730, including a plurality of workstation cards 732 and, optionally, one or more off-station responsibility cards 734. Each workstation card 732 may include a primary workstation identifier (ID). For example, the primary workstation ID, such as a workstation name and number (if multiple present in store configuration), may appear at the top of the card and be highlighted by font, color, formatting, or other indicators. Each workstation card 732 may include a staff identifier (ID), such as a name, to identify the staff person assigned to the workstation card. Each workstation card 732 may include a staff type indicator. For example, staff type may be indicated by a different color scheme, icon, or other visual indicator for pharmacists or technicians, such as pharmacist cards appearing in orange and technician cards appearing in blue. Each workstation card 732 may optionally include one or more secondary IDs, such as the names of other workstations. These secondary IDs may identify additional workstations and/or off-station tasks that the staff person assigned to the workstation card should also monitor and assist with as available, generally displayed in priority order. Off-station responsibility card(s) 734 may include one or more cards labelled "Off-Station" or with a similar identifier and listing one or more off-station tasks. In some embodiments, each off-station task may include a corresponding staff ID for the person assigned or each off-station responsibility card may include a single staff ID and list one or more off station tasks assigned to that individual (generally displayed in priority order). In some embodiments, workstation cards 732 may be displayed in a preferential order, such as placing the workstation card that includes the workstation it is being displayed on at the far left of configuration deck 730, and/or include a highlight or other visual indicator which card is most relevant to the assigned user at that workstation. In some embodiments, not all workstation cards 732 and/or off-station cards 734 may fit in the available display space and current assignment notification 720 may include a navigation option to display the undisplayed workstation cards, such as a scroll bar, arrows, or an additional workstations button 744.

Current assignment notification 720 may include one or more additional navigation options, such as buttons, menus, hot-keys, etc., that may initiate a new window or alternate interface for supporting additional work assignment interface tasks. For example, current assignment notification 720 may include a staffing override button 740, a full schedule button 742, and/or an additional workstations button 744.

Staffing override button 740 may initiate a window or similar interface for users with appropriate credentials to override the current assignments and reconfigure configuration deck 730 and/or the staff assignments therein. Full schedule button 742 may initiate a window or similar interface for navigating additional operating windows, such as past or future rotations, shifts, or days. For example, colleagues can click full schedule button 742 to see their suggested assignments for the day ahead. Additional workstations button 744 may initiate a window or larger overlay configuration that displays all workstation cards 732 and off-station responsibility cards 734 at once. Additional workstations button 744 may be selectively enabled only when all cards do not fit in the initial current assignment notification display area.

In some embodiments, current assignment notification 720 may include a notification icon and/or notification message area (not shown). The workstation assignment engine may include a messaging channel to feed a notification down to stores and provide a visual indicator that notification(s) are waiting, such as an icon that turns green when there is a notification available. In some embodiments, clicking on the icon may display the notification and/or clear the notification indicator. A new notification may be a trigger event for displaying current assignment notification 720. In some embodiments, the notification function may be used to further explain unscheduled staffing changes and/or publish backup requests.

Figure 8:
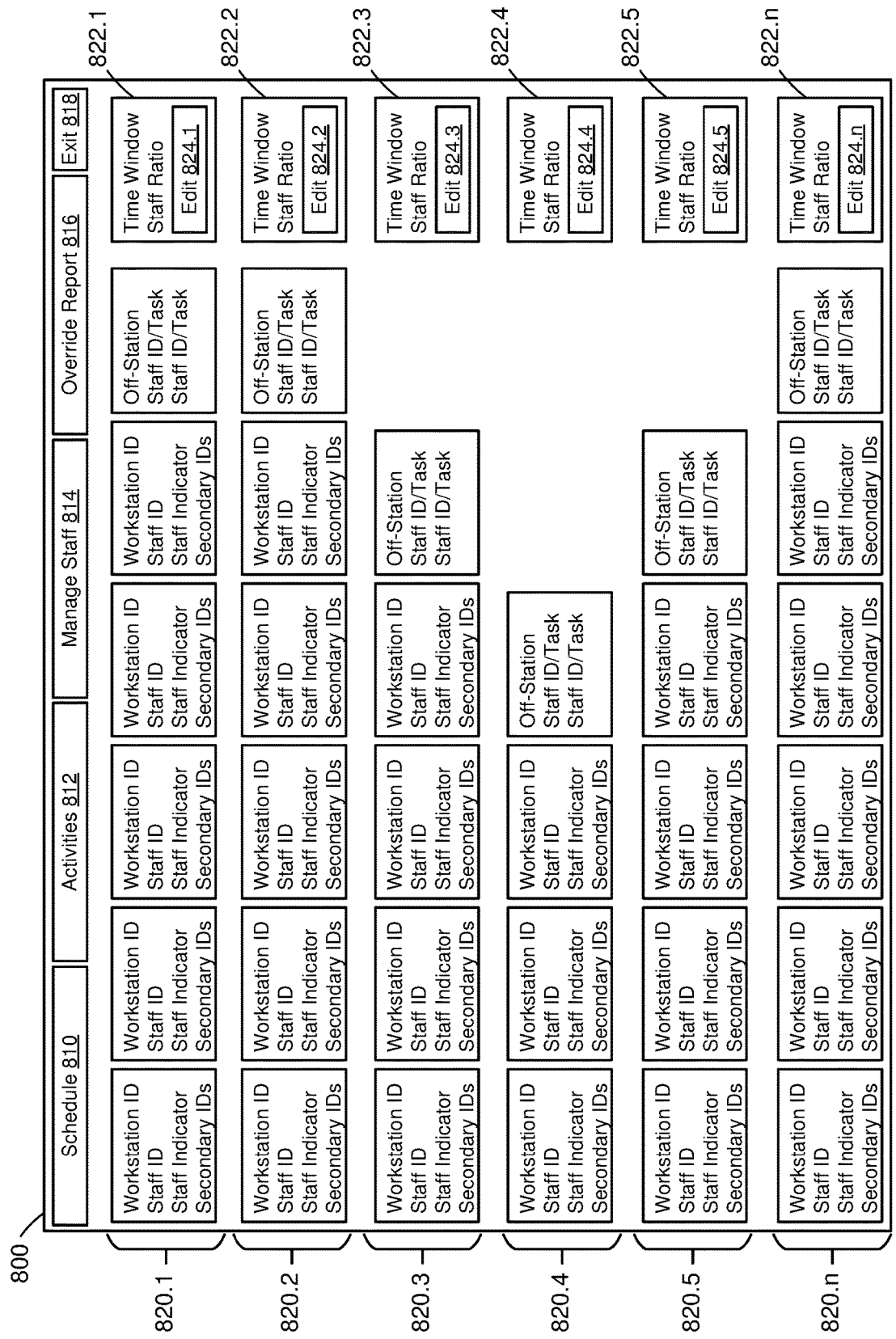
FIG. 8 is a block diagram of an example workstation interface configured to display and manage workstation assignments.

FIG. 8 shows an example graphical user interface for a pharmacy workstation terminal, such as a pharmacy computing system 104 in FIG. 1 or pharmacy computing system 200 in FIG. 2. Workstation display 800 may define some or all of a display area, such as monitor or a window displayed on a monitor, configured for displaying and managing configuration decks, employee assignments, and resulting schedules. For example, workstation display 800 may display suggested workstation assignments for the full day ahead (up to 24 hours) in an expanded workstation schedule, such as may be launched by full schedule button 742 or used for pharmacy scheduler 220. Future rotations may be configured based upon the employees that are expected to be in the pharmacy at that time (shift data being fed to the workstation assignment engine from the scheduling application feed). Configuration decks may take into account the workstation busy times. Workstation busy time data may be fed to the workstation assignment engine as described above and workstation busy times may be broken down by store, by workstation (pick up, drive thru, production, drop off), by day of week, by time of day, etc. and used for configuration deck selection and workstation assignments. Suggested configuration decks and assignments also take into account colleague proficiencies (high, med, low) at each workstation (proficiency data being fed to DEWA from proficiency data in the scheduling application feed).

Workstation display 800 may include navigation options for different functions that support viewing, managing, editing, or overriding the current schedule. For example, schedule tab 810 may relate to the present display of configuration decks organized by time window to provide a schedule for a shift, day, or similar time period. Schedule tab 810 may also include options for configuring the displayed schedule for different time periods, organization, or other options. Activities tab 812 may include a window that enables the user to review, edit, create, and delete activities, such as off-station tasks, for use in the schedule and configuration decks. In some embodiments, activities tab 812 may operate similar to the task configuration interface described below with regard to FIG. 9.

Manage staff tab 814 may include a window, screen, or other interface that enables the user to review the staff for the store, employment parameters relevant to scheduling and workstation assignments (job codes, types, competencies, proficiency ratings, hours available, etc.), etc. For example, manage staff tab 814 may be used to manage drop down lists of available employees, sorted by employee type (pharmacist, technician, etc.), that may be used for editing employee assignments for the schedule. In some embodiments, clicking the 'Manage Staff' tab allows store teams to make changes to colleague shifts or breaks. The information in the manage staff interface may be pulled from the scheduling application and reflect the shifts and suggested lunch break times. Users may edit the start or end time of a shift or lunch break, or completely remove/add a shift in order for the full day suggested schedule to be accurate in the event there is a real time change to the scheduling application data.

Override report tab 816 may include a window, screen, or other interface that enables the user review information describing override events for a selected time period. In some embodiments, override report tab 816 may also include other unscheduled staff change events, such as backup requests or automated reconfigurations due to late or missing staff. In some embodiments, clicking 'Override Report' will display the captured data from the past 90 days (or another configurable period) at the store level of the edits that have been made to rotations/assignments. For example, override report tab 816 may include a date and time for each event, a responsibility indicator for the authorizing staff or system condition that generated the change, and a description of the change or changes made. Workstation display 800 may include an exit button 818 for closing the expanded work assignment interface and returning to a prior screen or window on the workstation.

The majority of workstation display 800 may used to display a current schedule for the retail pharmacy. For example, a series of configuration decks 820.1-820.$n$ may be organized in time order according to their operating window to represent a larger unit of time, such as a shift, day, or multiple days. Each configuration deck 820 may represent the workstation and off-station responsibility assignments for each staff person scheduled at that time. For example, each configuration deck 820 may include a plurality of responsibility cards organized as workstation cards and off-station cards for a staff number and staff ratio scheduled for that time window. Each configuration deck 820 may have a corresponding configuration deck identifier 822.1-822.$n$ that uniquely identifies the assigned configuration deck by time window and staff ratio. Each configuration deck 820 may also have a corresponding edit button 824.1-824.$n$. In some embodiments, edit buttons 824 may open another interface, such as a popover or window, that includes an editing interface for the selected configuration deck. For example, the editing interface may include an option to edit card ratios and select a different configuration deck with a different staff ratio. The editing interface may include options for manually reconfiguring the configuration deck while keeping the same staff ratio. The editing interface may include options for selecting or changing employees assigned to each responsibility card (workstation card or off-station card). The editing interface may allow the user to save the edited configuration deck and employee assignments and the changes will be reflected in configuration decks 820. Users may have the ability to use the editing interface to indicate a staffing level change (edit card rotation), a workstation assignment swap (edit station assignment), or implementation of an off station task that needs to be executed (i.e. store delivery truck arrived late today and therefore, team needs it to be put away at a different time than usual). In some embodiments, the editing interface may be initiated by staffing override button 740 to edit the configuration deck and/or employee assignments for the current assignments in real-time and generate an override event.

Figure 9:
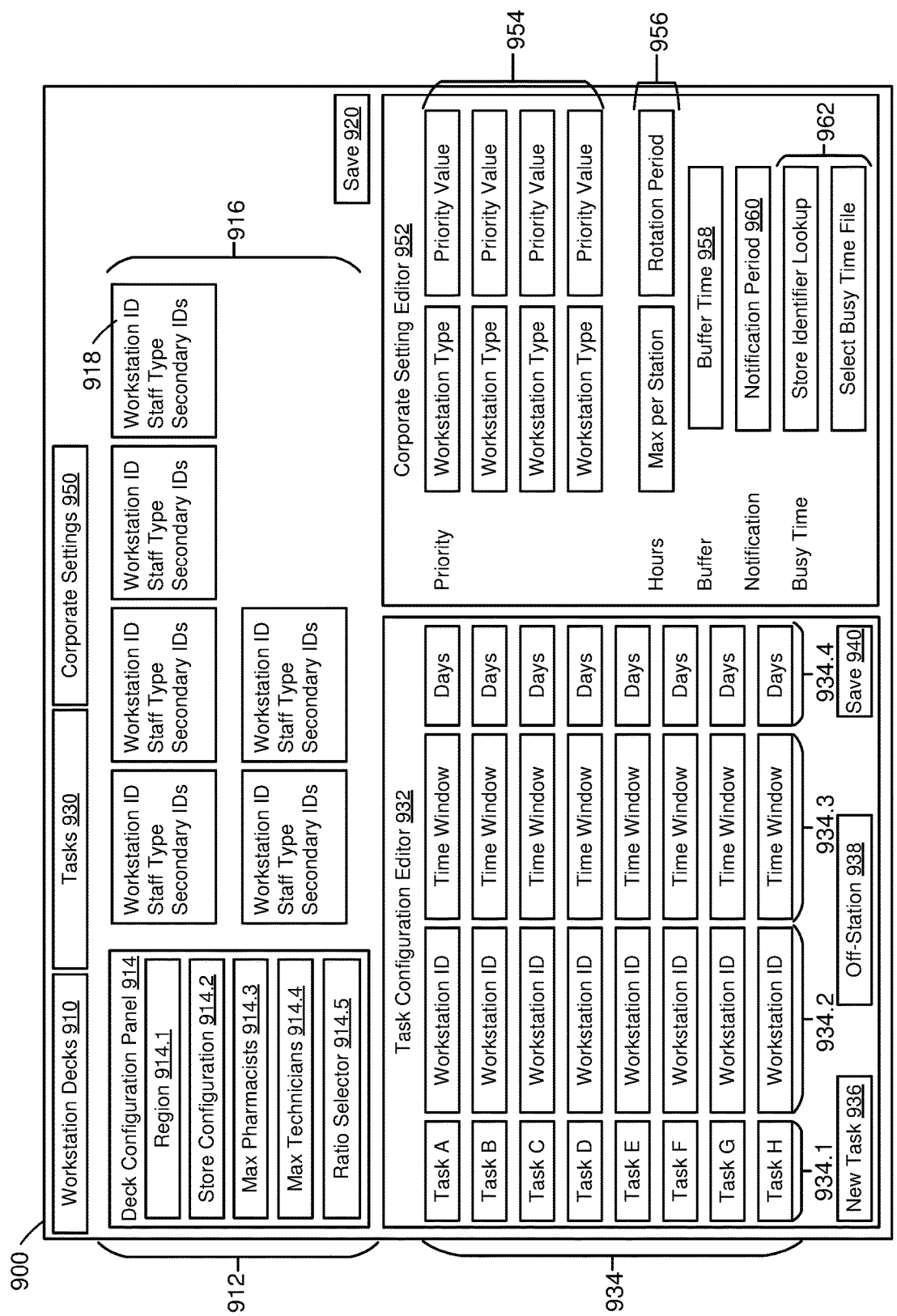
FIG. 9 is a block diagram of an example enterprise management interface configured to manage configuration decks and staffing rules.

FIG. 9 shows an example graphical user interface for a pharmacy workstation terminal, such as a pharmacy computing system 104 in FIG. 1 or pharmacy computing system 200 in FIG. 2, or a similarly configured corporate workstation for managing the workstation assignment engine. For example, the workstation configuration engine may include an enterprise configuration manager that supports a graphical user interface for managing workstation assignment configurations at the corporate level. In some embodiments, a dashboard and a number of interfaces may be provided for various configuration functions. Corporate users may use a dashboard interface to a corporate user database for backend setup of workstation assignment decks, on and off station tasks, and corporate configurable settings. For example, enterprise configuration manager interface 900 may include editors for workstation decks 910, tasks 930, and corporate settings 950.

Workstation decks 910 may initiate an interface for generating and storing configuration decks through a configuration deck editor 912. Configuration deck editor 912 may include configurability to load state specific, drive thru or non-drive thru, and other configurations of workstation assignment decks to use to generate workstation cards. In some embodiments, configuration deck editor 912 may include a deck configuration panel 914 to enable a user to define acceptable parameters for creating a new configuration deck. For example, region 914.1 and store configuration 914.2 may include drop-down menus to select the region or regions and the types of store configurations in which the configuration deck should include valid workstations and regulatory compliant staffing ratios and credentials. Region 914.1 may limit the staffing ratios to those compliant with local regulations and may define workstations and tasks that require pharmacist, technician, or other credentials. Store configuration 914.2 may include the presence or absence of a drive-thru, as well as the number of stations of each type that are available in the selected store configuration. Max pharmacists 914.3 and max technicians 914.4 may include drop down menus for selecting the maximum staffing levels that should be considered for generating the new configuration deck. Based on the maximum number of pharmacists and technicians and the regulatory requirements of the region, ratio selector 914.5 may enable the user select specific staffing ratios to use in generating a new configuration deck. In some embodiments, ratio selector 914.5 may generate a list of possible ratios and include visual indicators for ratios that are not usable due to regulatory compliance (or corporate policy or other applicable rules). For example, selection indicators, such as green check marks to enable or red circles to disable, may be used for enabling or disabling certain staffing level ratios that may be non-compliant with state regulations. A further visual indicator may be used to select the staff ratio to be used for generating the configuration deck.

Based on a selected staff ratio (which also defines total staff) from ratio selector 914.5, a set 916 of workstation cards 918 may be generated that includes a number of workstation cards 918 equal to the total staff and with staff types corresponding to the selected staff ratio. So, for example, a 2:4 pharmacist technician ratio may generate six workstation cards 918 with two cards pre-populated with a pharmacist staff type and four cards pre-populated with technician staff type. A corporate user may have the ability to edit the primary and secondary responsibilities for each of the different cards in the card ratios. For example, each primary and secondary responsibility field may include drop downs corresponding to the workstation types (and numbers) for allocating workstation responsibilities by workstation identifier (e.g., QA1, Drop Off 1, Production 1, etc.) among the different workstation cards 918. In some embodiments, corporate users may load and edit workstation decks and their components at any time, and this information may be fed to pharmacies on a daily basis for assigning employees to workstation rotations.

Tasks 930 may initiate an interface for generating and storing on-station and off-station tasks and schedules through a task configuration editor 932. Task configuration editor 932 may include configurability to set up on and off station tasks for use in pharmacies, responsibility cards, and employee assignments. Task configuration editor 932 may include a plurality of task definitions 934 (e.g. tasks A-H). For example, each task definition 934 may include a task name or identifier 934.1, a location identifier 934.2, a time window 934.3, and the days 934.4 on which the task should be completed. Location identifier 934.2 may include workstation identifiers for workstation tasks and "off-station" or specific off-station locations for off-station tasks. Example workstation identifiers may include numeric codes, text descriptors, and/or name strings, such as "Production 1", "Production 2", "Drop-Off", "Pick-Up", Drive-Thru", "Quality Assurance", etc. Time window 934.3 may include a start time and a stop time and, in some embodiments, a duration (that may or may not equal the entire time interval). Time window 934.3 may be configured to include multiple time windows and map different time windows to different days of the week. For example, tasks can be designated to be completed at different times during the weekdays vs. weekend days. Days 934.4 may enable tasks to be schedule for specific days of the week. For example, tasks can be designated to be completed on one or more days of the week/weekend. New task button 936 may add a new task and enable a user to edit each field of the corresponding task definition 934. Off-station button 938 may be an example of a filtering button that may enable the user to filter the tasks in task configuration 932 to a particular type, such as off-station versus on-station tasks. In some embodiments, off-station button 938 may also toggle context specific displays and drop down menus for the fields of task definitions 934. Save button 940 may enable the user to save the current list of tasks in task configuration editor 932. In some embodiments, corporate users may have the option to make all tasks or select tasks either editable or non-editable by store users. Users may be able to edit, remove, or add tasks at any time. Task definitions defined through task configuration editor 932 may be fed to pharmacies on a regular basis (e.g., daily).

Corporate settings 950 may initiate an interface for managing corporate settings through a corporate setting editor 932. Corporate setting editor 932 may include corporate database configurable settings. The selected values for each setting may be launched to all stores in the chain, and may be changed at any time. Corporate setting parameters may be fed to all pharmacies on a regular basis (e.g., daily).

Assignment priority 954 may include an interface for selecting the order in which the corporate user designates that each workstation should be assigned in the event there are not 4 colleagues to fill all 4 primary workstations. (i.e. if there is only 1 RPh and 2 technicians, assign those technicians to drop off then drive thru based on the assignment priority the corporate user has designated). Each workstation type may be assigned a unique priority value (e.g. 1-4) to determine the order in which they should be assigned.

Station Hours Settings 956 may include an interface for selecting hours parameters for employees assigned to workstations. For example, maximum per station may designate the maximum number of hours a colleague should spend at one workstation on a daily basis and rotation period may designate the number of hours within a rotation period (i.e. 8 am-10 am, 10 am-noon, noon-2 pm).

Rotation buffer time 958 may include an interface to designate the number of minutes for the 'buffer time' (i.e. the number of minutes before or after the start of a new rotation period allowing colleagues X number of minutes to punch in/out either early or late (i.e. if rotation period begins at 8 am, 5 minutes buffer would allow for a window of 7:55 am-8:05 am for colleagues to punch in/out as their shift is beginning or ending).

Notification Period 960 may include an interface to designate the number of seconds for the notification that pops from the bottom of the screen to display before then disappearing.

Busy time 962 may include an interface to allow a user to upload a 'busy time' file as often as necessary for each store, organized by store identifier. For example, a busy file may designate the 2 busiest hours at each workstation on each day of the week. A store identifier lookup may allow the user to determine whether a busy file has been uploaded for a specific store and how recent that busy file is and select busy time file may allow the user to select a new or updated busy time file for the store identifier. In some embodiments, busy time files may automatically be updated from a corporate analytics data store that uses historic transaction analysis to identify business patterns for specific stores. For example, store 123 may be identified as busiest at the pick up workstation on Mondays from 8 am-9 am and 4 pm-5 pm based on historic transaction data for store 123. In some embodiments, as described above, busy time information may be tied to the colleague proficiency data to determine employee assignments to specific workstations at specific times. For example, a colleague with high proficiency at pick up at store 123 may be assigned to pick up on Mondays from 8 am-9 am and 4 pm-5 pm.

Figure 10:
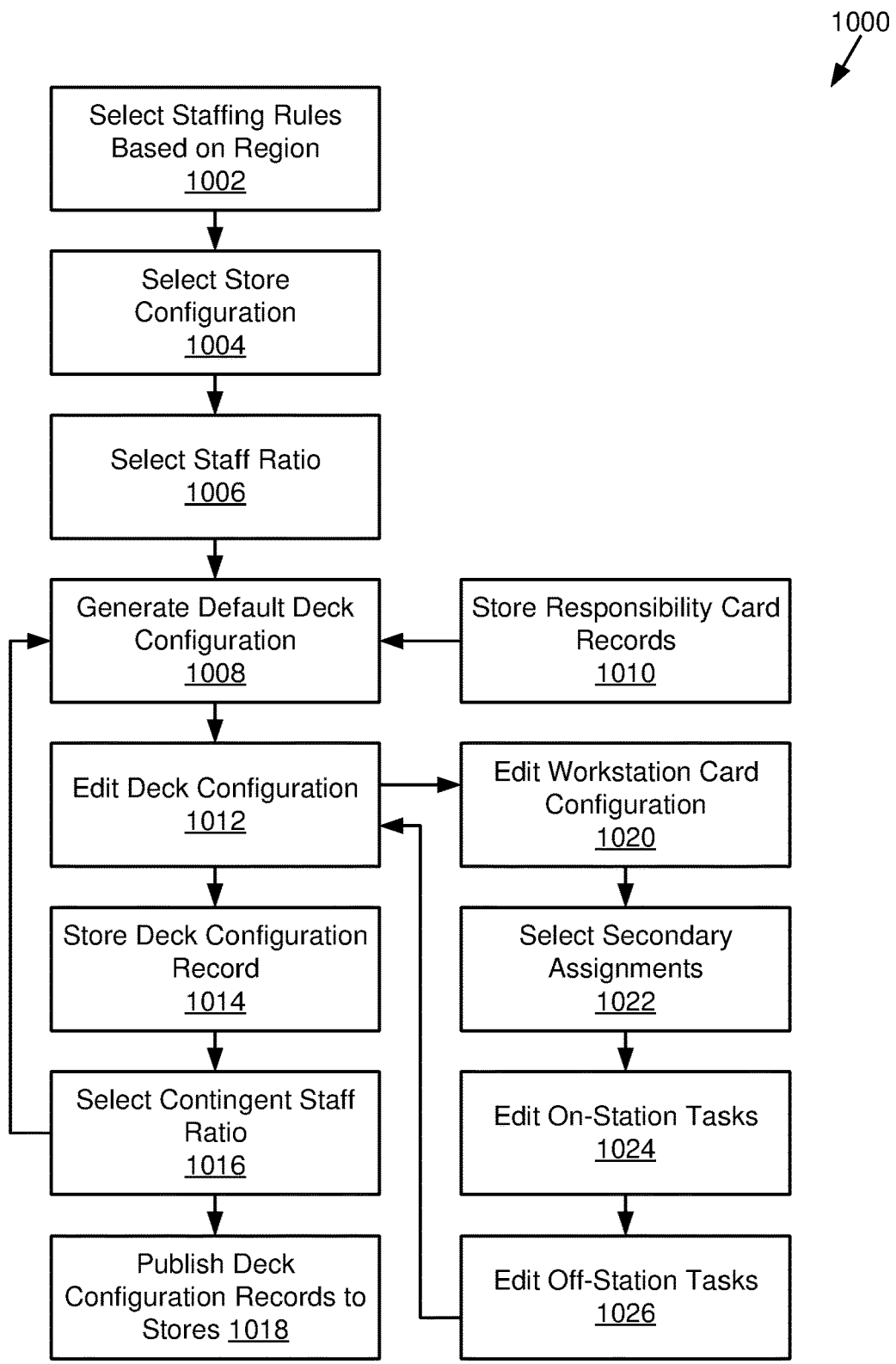
FIG. 10 is a flowchart of an example method of generating configuration decks.

FIG. 10 shows an example method 1000 of generating configuration decks. For example, pharmacy information system 100 of FIG. 1 and/or pharmacy computing system(s) 200 of FIG. 2 may be operated in accordance with blocks 1002-1026 of method 1000 to generate responsibility cards and configure them configuration decks for use by the workstation assignment engine and pharmacy users. In some embodiments, an interface similar to enterprise configuration manager interface 900 may be used for method 1000.

At block 1002, staffing rules may be selected based on region. For example, a user may select a region in which the resulting configuration deck may be used and the region may identify the staffing rules, such as acceptable ratios and staff types for workstations and tasks, to be enforced by a configuration deck editor.

At block 1004, a store configuration may be selected. For example, the user may select a store configuration for which the resulting configuration deck may be used and the store configuration may identify the workstations available within that store configuration and to be used in the configuration deck editor.

At block 1006, a staff ratio may be selected. For example, the user may select a staff ratio from the possible staff ratios based on staffing rules and a maximum number of pharmacists and technicians that may reasonably be staffing the target stores.

At block 1008, a default deck configuration deck may be generated. For example, an assignment generator may populate a set of workstation responsibility cards with primary workstation responsibilities based on the staff ratios and workstation priority logic. In some embodiments, a plurality of responsibility card records may have been stored for use in generating default deck configurations at block 1010. For example, workstation responsibility cards that correspond to primary workstation assignments for each workstation type in the store configuration may be available to the assignment generator.

At block 1012, the deck configuration may be edited. For example, the user may use a deck configuration editor to modify primary workstation responsibilities, add secondary workstation responsibilities, and/or add on-station or off-station tasks. An example editing process is further described with regard to blocks 1020-1026.

At block 1014, the deck configuration may be stored. For example, the user may store the deck configuration in a deck configuration record in a corporate data store.

At block 1016, a contingent staff ratio may be selected. For example, the user may select a staff ratio that represents one or more staff being unavailable. Method 1000 may return to block 1008 to generate a contingent deck configuration and may repeat this process until as many contingent deck configurations are defined as may be desired and both the original deck configuration and contingent deck configurations are stored as deck configuration records.

At block 1018, the deck configuration records may be published to the stores. For example, deck configuration records may be published to the stores daily and become active for use by assignment generators, pharmacy schedulers, and override operations.

At block 1020, the workstation card configuration may be edited. For example, the user may use the deck configuration editor to change primary workstation assignments.

At block 1022, secondary workstation assignments may be selected for one or more workstation cards. For example, the user may use the deck configuration editor to add secondary workstation assignments to any of the workstation responsibility cards.

At block 1024, on-station tasks may be edited. For example, the user may use the deck configuration editor to add or modify one or more on-station tasks associated with one or more of the workstations in the primary or secondary workstation responsibilities.

At block 1026, off-station tasks may be edited. For example, the user may use the deck configuration editor to add or modify one or more off-station tasks for use in managing off-station tasks and the generation of off-station responsibility cards.

Figure 11:
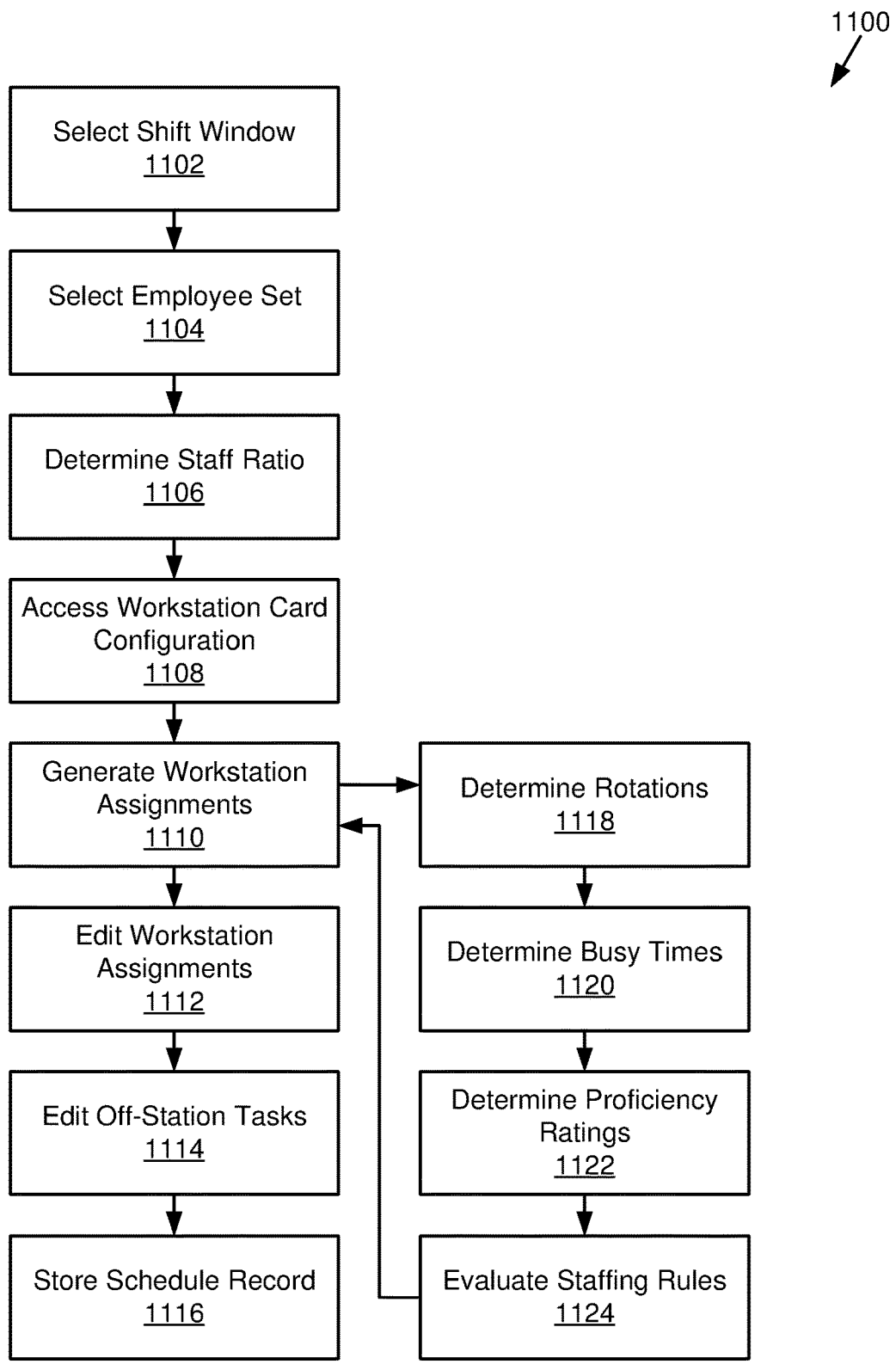
FIG. 11 is a flowchart of an example method of scheduling workstation assignments using configuration decks.

FIG. 11 shows an example method 1100 of scheduling employee assignments to responsibility cards in configuration decks. For example, pharmacy information system 100 of FIG. 1 and/or pharmacy computing system(s) 200 of FIG. 2 may be operated in accordance with blocks 1102-1124 of method 1100 to assign employees to responsibility cards and store them in a schedule record for use in pharmacy operations.

At block 1102, a shift window may be selected. For example, a pharmacy scheduler may be used to select a shift window to be scheduled.

At block 1104, an employee set may be selected. For example, the pharmacy scheduler may determine or select an employee set from the employees associated with the store identifier for the store being scheduled.

At block 1106, a staff ratio may be determined. For example, the pharmacy scheduler may use a staff ratio based on historical staffing, budget, or another defined or dynamically generated staffing level for the shift and store being scheduled.

At block 1108, a workstation card configuration may be accessed. For example, the pharmacy scheduler may load a previously generated configuration deck record for the store configuration and staffing level, such as a configuration deck record generated using method 1000.

At block 1110, workstation assignments may be generated. For example, an assignment generator may assign employees from the employee set to the responsibility cards in the accessed configuration deck. In some embodiments, additional blocks for generating workstation assignments may be processed at blocks 1118-1124.

At block 1112, workstation assignments may be edited. For example, a user may use the pharmacy scheduler to modify the system generated workstation assignments based on specific knowledge of personal schedules, requests and preferences of staff, anticipated tasks or busy times not reflected in the current records, etc.

At block 1114, off-station tasks may be edited. For example, the user may add, remove, move, or modify off-station tasks to better align with anticipated staffing and needs.

At block 1116, a schedule record may be stored for the shift window. For example, the pharmacy scheduler may store the schedule record comprised of time-based sets of assigned responsibility cards and the stored records may be available to pharmacy staff to anticipate workstation assignments for current and future shifts and rotations.

At block 1118, rotations may be determined. For example, a corporate rotation parameter may be used by the pharmacy scheduler to break shifts into rotation increments, such as two-hour operating periods.

At block 1120, busy times may be determined. For example, a busy time record may be accessed by the pharmacy scheduler that identifies busy times for one or more workstations.

At block 1122, proficiency ratings for the staff in the employee set may be determined. For example, the pharmacy scheduler may access proficiency ratings for each employee that identify their comparative proficiency at the various workstations.

At block 1124, staffing rules may be evaluated for automatically generate the workstation assignments at block 1110. For example, a set of logical rules may use the busy times and staff proficiency rating to assign the most proficient staff to the busy times in relevant workstations while also managing maximum time on station, breaks and lunches, off-station tasks, and other constraints for assignment responsibility cards from the configuration deck.

Figure 12:
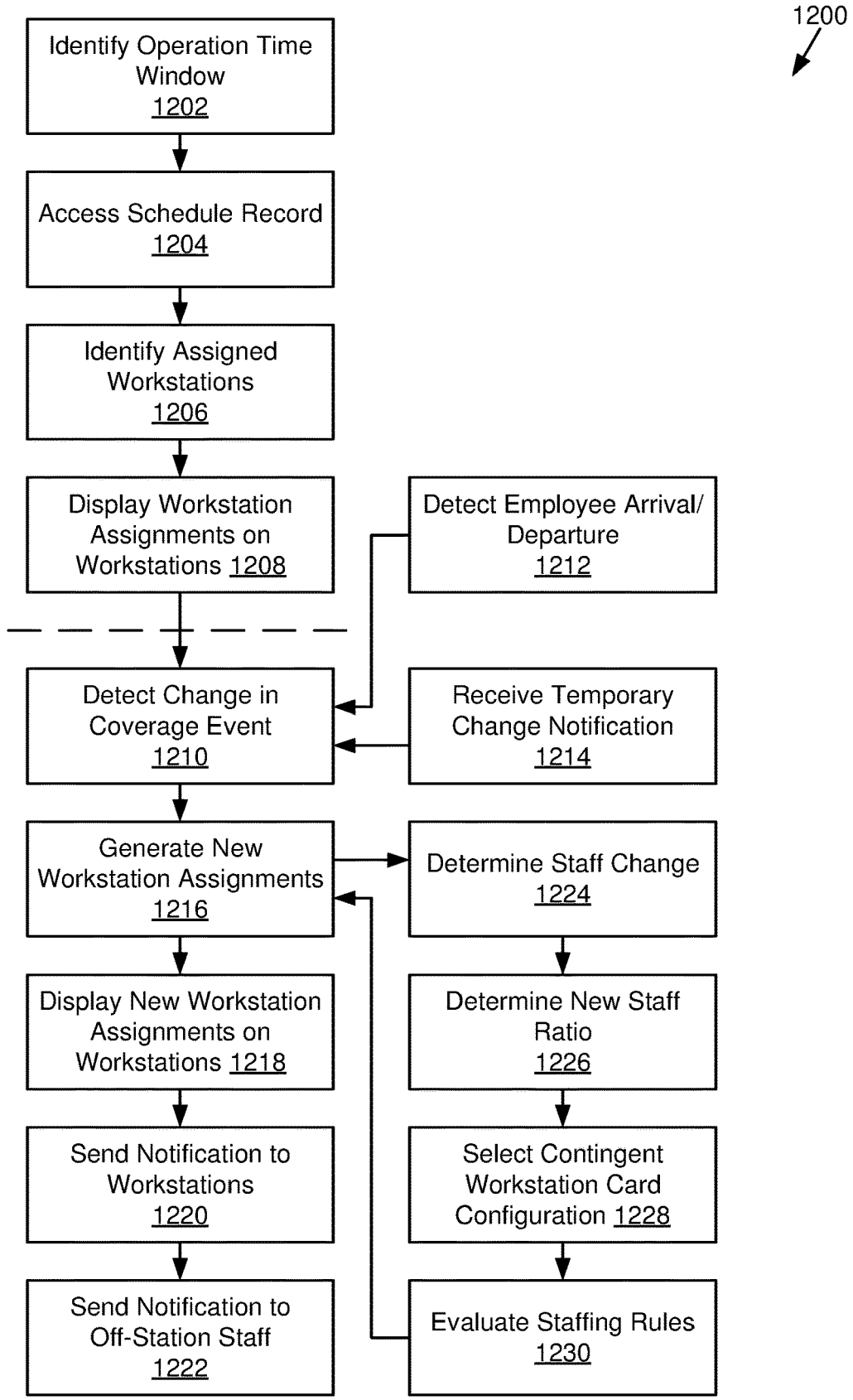
FIG. 12 is a flowchart of an example method of displaying and dynamically modifying workstation assignments.

FIG. 12 shows an example method 1200 of dynamically generating employee assignments to responsibility cards in configuration decks. For example, pharmacy information system 100 of FIG. 1 and/or pharmacy computing system(s) 200 of FIG. 2 may be operated in accordance with blocks 1202-1230 of method 1200 to assign employees to responsibility cards in response to change events during pharmacy operations.

At block 1202, an operation time window may be identified. For example, the pharmacy scheduler may define a rotation time window within a scheduled shift.

At block 1203, a schedule record may be accessed. For example, the workstation assignment engine may access the schedule record for the current operation time window.

At block 1206, assigned workstations may be identified. For example, the responsibility card assignments for the scheduled configuration deck may be read from the schedule record.

At block 1208, the current workstation assignments may be displayed on workstations. For example, the workstation overlay generator may generate an assignment overlay to be displayed at the workstations on demand or based on rotations or change events. In some cases, blocks 1202-1208 may operate through each rotation in a shift without proceeding to the other blocks of method 1200. But eventually, a shift change or other staffing change event may trigger additional blocks of method 1200.

At block 1210, a change in coverage event may be detected. For example, a staffing change service may detect a change in coverage from one or more sources. At block 1212, an employee arrival or departure may be detected from a timesheet service or related clock-in or clock-out events. At block 1214, a temporary change notification may be received, such as a backup request, manual override, or similar event.

At block 1216, new workstation assignments may be generated. For example, an assignment generator may generate new workstation assignments by assigning employees to different responsibility cards in the same configuration deck or a new configuration deck based on reduced staffing levels, changed staff ratios, and/or forced allocation of workstation or off-station responsibilities.

At block 1218, the new workstation assignments may be displayed on the workstations. For example, the workstation overlay generator may generate a new workstation overlay reflecting the new responsibility card assignments in the configuration deck and push the workstation overlay contents to the work assignment interface for each workstation.

At block 1220, a notification may be sent to the workstations. For example, some changes may be accompanied by a notification message that provides an explanation of the change, such as a backup request message.

At block 1222, the notification and/or new workstation assignments may be sent to off-station staff. For example, off-station staff may have an associated mobile device with an application supporting a mobile work assignment interface and the new workstation assignments and/or notification message may be provided to the mobile devices.

At block 1224, a staff change may be determined. For example, the staffing change service may determine fewer staff than scheduled are present for a shift.

At block 1226, a new staff ratio may be determined. For example, the staffing change service may determine different staff ratio based on the staff actually present according to the clock-in and clock-out events.

At block 1228, a contingent workstation card configuration may be selected. For example, the workstation assignment engine may have stored one or more contingent configuration decks corresponding to one or more reduced staffing levels and associated staff ratios. The new staff ratio may be used to select the contingent configuration deck that corresponds to that new staff ratio.

At block 1230, staffing rules may be evaluated. For example, the assignment engine may evaluate to staffing rules based on the reduced set of clocked-in staff and the contingent configuration deck to assign responsibility cards.

In one example use of the foregoing systems and methods, at the start of a rotation period, all pharmacy terminals will automatically display a pop notification from the bottom of the screen, lasting for X (configurable value) seconds, then disappearing again. Users are able to continue working through the X second pop duration. The 'on station' task "Day 14" may be displayed on the "Pick Up 1" assignment. This is a result of the task being previously setup and designated to display on the card during this specific timeframe. Clicking the "view full schedule" button will display all of the suggested 2-hour rotation cards for the day ahead. These card assignments are suggested based on the colleagues that are expected to be in the pharmacy at those times, and this information is fed to the workstation configuration engine from the scheduling tool.

In another example, there are colleagues with a red exclamation point and colleagues with a green check mark next to their workstation names in the popup notification. This is meant to be a visual indicator of whether or not the colleague has punched in at the POS system yet. There is communication between colleague punch data at POS and the workstation configuration engine allowing for distinguishing between those colleagues that are expected to be working, but have not yet punched in vs. those colleagues that are expected to be working and have already punched in. A configurable value, "buffer time", is X minutes allowing for colleagues to punch in or out a few minutes early or late (as we know this is an everyday occurrence). At the end of the buffer time, if the colleague has not punched in, a pop notification would display removing that colleague from the card completely. For example, Iain, Tina, Sachin, Rik, and Derek are all expected in and have punched in already. However, Caroline is expected in and has not yet punched in. She will be removed from the card completely after X minutes, or the end of the "buffer time". This may trigger an automatic reassignment of responsibilities based on the adjusted staff ratio and a contingent configuration deck.

At any time, store users may have an opportunity to make changes to a rotation card. Clicking the green edit button may then display the edit options for a card. Store users have the opportunity to change the number of staff in the pharmacy (ratio), station assignments, or off-station tasks. Those changes would then be reflected onto the rotation card. In this example, we can add an off-station task of Truck which would then be displayed on the card.

Store users may have the capability to add in custom on or off station tasks that have not already been entered by corporate users. For example, a store may choose to add waiting bin day 14 to their weekend on station tasks. Since they have customized the task to be tied to pick up 1 from 8 am-10 am, the task would then display on the card rotation under Iain's responsibilities (since he is assigned to pick up 1 during that operating window).

In some embodiments, alerts may be used to reinforce system management tasks, changes in assignments, and need for backup. After a certain amount of time without updating proficiencies, an alert may notify the pharmacy manager to have a development conversation with their staff and update proficiencies, as necessary. Pharmacy managers should be encouraged to get their colleagues to the highest proficiency in each workstation.

If a station requires back up, the system may alert their backup to assist them, particularly at customer facing stations such as pick up and drop off. These notifications may include push notifications to the pharmacy workstation where their backup is currently assigned and/or may include notifications through other devices associated with the backup person, such as a text message to their mobile phone. Similarly, when the system detects that a station is falling behind based on their task queue "going red", the system may automatically initiate backup notifications without requiring intervention from another user. In some configurations, a laser beam or similar detector may be used to detect the number of people standing and waiting at the drop-off and/or pick-up workstations, then automatically alert the system to notify back up.

Alerts may also be provided for specific tasks associated with a station that should be given priority. Important alerts may come up within the workstation assignment interface for completion by staff. For example, task assignments for recalls, MCC, and HUB tasks to be completed on a particular date may be displayed and then disappear when no longer relevant.

Alerts may be used for notifying teams if they have reached usage limits or have underutilized staff time for specific tasks. Hour usage trends may be tracked against weekly demand hours and the teams may be alerted if they have gone over. In some configurations, tasks that have exceeded allowed hours for the week will no longer appear in the task assignments for the appropriate workstations or off-station tasks. The alert may include the ability of the team to see how many hours they have left to allocate to a colleague for a specific task (if hours are unutilized).

Alerts may be used to identify colleagues without proper licensing to follow compliance being assigned to or engaging in certain tasks. In some configurations, staff without proper licenses may be locked out from a particular station. For example, any non-licensed/certified colleague may not be allowed to work behind the pharmacy counter. This will matter in particular in states with more restrictive laws.

Machine learning may be used to further enhance the workstation assignment engine and ensure that staff utilization and development are maximized. Data generated by the pharmacy dashboard or pharmacy task manager may be used to predict demand at various workstations and factor into real-time adjustments to workstation assignments and backup notifications. The workstation configuration engine may include machine learning algorithms for improving the volume predictions used by the scheduler for setting staffing levels. Both historical and real-time pharmacy task manager and pharmacy point-of-sale data may be used to train and adjust these algorithms. In addition, more advanced and multivariable algorithms for assigning specific workstations and tasks that align with individual staff proficiency and/or training needs may be implemented. For example, the system may include the ability to distinguish different job codes and colleague certifications to appropriately assign workstations and additional task. (i.e. Inventory specialist will be given inventory task with option to reassign, clerk/cashier will only be assigned to pick up work station, PTCB/ExCPT/ interns are able to do additional task that other staff may not be able to, etc.).

While the examples provided have been in the context of a retail pharmacy, other applications of the described systems and methods are also possible. For example, workstation allocation and related task management could be applied to retail store (or pharmacy "front store") operations or retail clinic operations. Other applications may include mail order pharmacies, long term care pharmacies, etc.

While at least one exemplary embodiment has been presented in the foregoing detailed description of the technology, it should be appreciated that a vast number of variations may exist. It should also be appreciated that an exemplary embodiment or exemplary embodiments are examples, and are not intended to limit the scope, applicability, or configuration of the technology in any way. Rather, the foregoing detailed description will provide those skilled in the art with a convenient road map for implementing an exemplary embodiment of the technology, it being understood that various modifications may be made in a function and/or arrangement of elements described in an exemplary embodiment without departing from the scope of the technology, as set forth in the appended claims and their legal equivalents.

As will be appreciated by one of ordinary skill in the art, various aspects of the present technology may be embodied as a system, method, or computer program product. Accordingly, some aspects of the present technology may take the form of an entirely hardware embodiment, an entirely software embodiment (including firmware, resident software, micro-code, etc.), or a combination of hardware and software aspects that may all generally be referred to herein as a circuit, module, system, and/or network. Furthermore, various aspects of the present technology may take the form of a computer program product embodied in one or more computer-readable mediums including computer-readable program code embodied thereon.

Any combination of one or more computer-readable mediums may be utilized. A computer-readable medium may be a computer-readable signal medium or a physical computer-readable storage medium. A physical computer readable storage medium may be, for example, but not limited to, an electronic, magnetic, optical, crystal, polymer, electromagnetic, infrared, or semiconductor system, apparatus, or device, etc., or any suitable combination of the foregoing. Non-limiting examples of a physical computer-readable storage medium may include, but are not limited to, an electrical connection including one or more wires, a portable computer diskette, a hard disk, random access memory (RAM), read-only memory (ROM), an erasable programmable read-only memory (EPROM), an electrically erasable programmable read-only memory (EEPROM), a Flash memory, an optical fiber, a compact disk read-only memory (CD-ROM), an optical processor, a magnetic processor, etc., or any suitable combination of the foregoing. In the context of this document, a computer-readable storage medium may be any tangible medium that can contain or store a program or data for use by or in connection with an instruction execution system, apparatus, and/or device.

Computer code embodied on a computer-readable medium may be transmitted using any appropriate medium, including but not limited to, wireless, wired, optical fiber cable, radio frequency (RF), etc., or any suitable combination of the foregoing. Computer code for carrying out operations for aspects of the present technology may be written in any static language, such as the C programming language or other similar programming language. The computer code may execute entirely on a user's computing device, partly on a user's computing device, as a stand-alone software package, partly on a user's computing device and partly on a remote computing device, or entirely on the remote computing device or a server. In the latter scenario, a remote computing device may be connected to a user's computing device through any type of network, or communication system, including, but not limited to, a local area network (LAN) or a wide area network (WAN), Converged Network, or the connection may be made to an external computer (e.g., through the Internet using an Internet Service Provider).

Various aspects of the present technology may be described above with reference to flowchart illustrations and/or block diagrams of methods, apparatus, systems, and computer program products. It will be understood that each block of a flowchart illustration and/or a block diagram, and combinations of blocks in a flowchart illustration and/or block diagram, can be implemented by computer program instructions. These computer program instructions may be provided to a processing device (processor) of a general purpose computer, special purpose computer, or other programmable data processing apparatus to produce a machine, such that the instructions, which can execute via the processing device or other programmable data processing apparatus, create means for implementing the operations/acts specified in a flowchart and/or block(s) of a block diagram.

Some computer program instructions may also be stored in a computer-readable medium that can direct a computer, other programmable data processing apparatus, or other device(s) to operate in a particular manner, such that the instructions stored in a computer-readable medium to produce an article of manufacture including instructions that implement the operation/act specified in a flowchart and/or block(s) of a block diagram. Some computer program instructions may also be loaded onto a computing device, other programmable data processing apparatus, or other device(s) to cause a series of operational steps to be performed on the computing device, other programmable apparatus or other device(s) to produce a computer-implemented process such that the instructions executed by the computer or other programmable apparatus provide one or more processes for implementing the operation(s)/act(s) specified in a flowchart and/or block(s) of a block diagram.

A flowchart and/or block diagram in the above figures may illustrate an architecture, functionality, and/or operation of possible implementations of apparatus, systems, methods, and/or computer program products according to various aspects of the present technology. In this regard, a block in a flowchart or block diagram may represent a module, segment, or portion of code, which may comprise one or more executable instructions for implementing one or more specified logical functions. It should also be noted that, in some alternative aspects, some functions noted in a block may occur out of an order noted in the figures. For example, two blocks shown in succession may, in fact, be executed substantially concurrently, or blocks may at times be executed in a reverse order, depending upon the operations involved. It will also be noted that a block of a block diagram and/or flowchart illustration or a combination of blocks in a block diagram and/or flowchart illustration, can be implemented by special purpose hardware-based systems that may perform one or more specified operations or acts, or combinations of special purpose hardware and computer instructions.

While one or more aspects of the present technology have been illustrated and discussed in detail, one of ordinary skill in the art will appreciate that modifications and/or adaptations to the various aspects may be made without departing from the scope of the present technology, as set forth in the following claims.

What is claimed is:

1. A system comprising:
a processor;
a memory;
a data store configured to store a plurality of staffing configuration deck records, wherein:
each staffing configuration deck record indicates a set of responsibility card records;
each responsibility card record comprises a workstation identifier and a staff type indicator; and
the set of responsibility card records corresponds to a staff ratio for that staffing configuration deck record; and
a configuration manager interface configured to:
identify a set of staff ratios corresponding to a store configuration identifier, wherein the set of staff ratios includes a plurality of staff ratios representing different combinations of employee numbers and employee types for possible staffing configurations for a set of workstation identifiers for the store configuration identifier;
automatically generate, for each staff ratio in the set of staff ratios, at least one staffing configuration deck record corresponding to that staff ratio;
publish a set of staffing configuration deck records to a plurality of retail stores corresponding to the store configuration identifier;
receive a selected staff ratio;
automatically determine, from the set of staffing configuration deck records, a default staffing configuration deck record comprised of a first set of responsibility card records corresponding to the selected staff ratio, wherein automatically determining the default staffing configuration deck record comprises automatically evaluating, using a rules engine, a set of rules corresponding to the store configuration identifier and the selected staff ratio to determine the first set of responsibility card records selected from the set of staffing configuration deck records; and
store the default staffing configuration deck record to the data store, wherein a scheduler service accesses the default staffing configuration deck record for assigning staff to each responsibility card record of the first set of responsibility card records for an operation window to generate a work schedule.

2. The system of claim 1, wherein the configuration manager interface is further configured to:
receive a contingent staff ratio;
automatically determine, from the set of staffing configuration deck records, a contingent staffing configuration deck record comprised of a second set of responsibility card records corresponding to the contingent staff ratio and the store configuration identifier; and
store the contingent staffing configuration deck record to the data store, wherein a scheduler service accesses the contingent staffing configuration deck record for assigning staff to each responsibility card record of the second set of responsibility card records for the operation window to generate the work schedule.

3. The system of claim 2, further comprising:
a plurality of electronic workstation displays configured to:
display a pharmacy workstation interface configured for completing workstation tasks;
automatically display, in current assignment overlays that obscure at least a portion of each pharmacy workstation interface, a first set of workstation assignments during a first operation time window, wherein the first set of workstation assignments correspond to the default staffing configuration deck record; and
automatically replace, in updated current assignment overlays that obscure at least a portion of each pharmacy workstation interface, the first set of workstation assignments with a second set of workstation assignments during the first operation time window and responsive to a change in coverage event, wherein the second set of workstation assignments correspond to the contingent staffing configuration deck record.

4. The system of claim 1, wherein:
the configuration manager interface is further configured to:
determine, for at least one responsibility card record in the first set of responsibility card records, a secondary assignment; and
add a workstation identifier for the secondary assignment to the at least one responsibility card record prior to storing the default staffing configuration deck record; and
the at least one responsibility card record has a primary workstation identifier that is different than the workstation identifier for the secondary assignment.

5. The system of claim 1, wherein:
the configuration manager interface is further configured to:
receive, for at least one responsibility card record in the first set of responsibility card records, at least one task identifier; and
add the at least one task identifier to the at least one responsibility card record prior to storing the default staffing configuration deck record; and
the at least one task identifier corresponds to a task workstation identifier and a time window for completing that task assignment.

6. The system of claim 1, wherein:
the configuration manager interface is further configured to determine a set of staffing rules based on a geographic region;
the set of rules comprises the set of staffing rules applied to the store configuration identifier and the selected staff ratio; and
the set of workstation identifiers for the store configuration identifier corresponds to a number of workstations of each type of workstation in at least one retail store.

7. The system of claim 1, further comprising:
a scheduling service configured to:
receive the default staffing configuration deck record;
select specific employees for each responsibility card record of the first set of responsibility card records; and
generate a first set of workstation assignments for a first operation time window, wherein a plurality of workstation interface displays is configured to display the first set of workstation assignments to a user of each workstation interface display of the plurality of workstation interface displays.

8. The system of claim 1, wherein the configuration manager interface is further configured to:
select a set of staffing rules to be applied to selecting among the set of staffing configuration deck records to automatically determine the default staffing configuration deck record.

9. The system of claim 8, further comprising:
an assignment generator configured to:
- access the set of staffing configuration deck records and the set of staffing rules for a selected store based on the store configuration identifier; and
- use the set of staffing configuration deck records and the set of staffing rules for selection of workstation assignments for a plurality of operation time windows.

10. The system of claim 9, further comprising:
at least configured one workstation display interface configured to display, for each operation time window of the plurality of operation time windows:
- a time window identifier for that operation time window;
- a staff ratio identifier for that operation time window; and
- a staffing configuration deck for that operation time window and corresponding configuration deck record, wherein each responsibility card record in that staffing configuration deck record is populated with a staff identifier for an employee assigned to that responsibility card record.

11. A computer-implemented method comprising:
identifying a set of staff ratios corresponding to a store configuration identifier, wherein the set of staff ratios includes a plurality of staff ratios representing different combinations of employee numbers and employee types for possible staffing configurations for a set of workstation identifiers for the store configuration identifier;
automatically generating, for each staff ratio in the set of staff ratios, at least one staffing configuration deck record corresponding to that staff ratio;
publishing a set of staffing configuration deck records to a plurality of retail stores corresponding to the store configuration identifier;
receiving a selected staff ratio;
automatically determining, from the set of staffing configuration deck records, a default staffing configuration deck record comprised of a first set of responsibility card records corresponding to the selected staff ratio, wherein automatically determining the default staffing configuration deck record comprises automatically evaluating, using a rules engine, a set of rules corresponding to the store configuration identifier and the selected staff ratio to determine the first set of responsibility card records selected from the set of staffing configuration deck records;
storing the default staffing configuration deck record in a data store, wherein:
- the default staffing configuration deck record indicates the first set of responsibility card records;
- each responsibility card record comprises a workstation identifier and a staff type indicator; and
- the first set of responsibility card records corresponds to the selected staff ratio for that staffing configuration deck record; and
accessing the default staffing configuration deck record for assigning staff to each responsibility card record of the first set of responsibility card records for an operation window to generate a work schedule.

12. The computer-implemented method of claim 11, further comprising:
receiving a contingent staff ratio;
automatically determining, from the set of staffing configuration deck records, a contingent staffing configuration deck record comprised of a second set of responsibility card records corresponding to the contingent staff ratio and the store configuration identifier;
storing the contingent staffing configuration deck record in the data store; and
accessing the contingent staffing configuration deck record for assigning staff to each responsibility card record of the second set of responsibility card records for the operation window to generate the work schedule.

13. The computer-implemented method of claim 12, further comprising:
displaying, on a plurality of electronic workstation displays, a pharmacy workstation interface configured for completing workstation tasks;
automatically displaying, in current assignment overlays that obscure at least a portion of each pharmacy workstation interface, a first set of workstation assignments during a first operation time window, wherein the first set of workstation assignments correspond to the default staffing configuration deck record; and
automatically replacing, in updated current assignment overlays that obscure at least a portion of each pharmacy workstation interface, the first set of workstation assignments with a second set of workstation assignments during the first operation time window and responsive to a change in coverage event, wherein the second set of workstation assignments correspond to the contingent staffing configuration deck record.

14. The computer-implemented method of claim 11, further comprising:
determining, for at least one responsibility card record in the first set of responsibility card records, a secondary assignment; and
adding a workstation identifier for the secondary assignment to the at least one responsibility card record prior to storing the default staffing configuration deck record, wherein the at least one responsibility card record has a primary workstation identifier that is different than the workstation identifier of the secondary assignment.

15. The computer-implemented method of claim 11, further comprising:
receiving, for at least one responsibility card record in the first set of responsibility card records, at least one task identifier; and
adding the at least one task identifier to the at least one responsibility card record prior to storing the default staffing configuration deck record, wherein the at least one task identifier corresponds to a task workstation identifier and a time window for completing that task assignment.

16. The computer-implemented method of claim 11, further comprising:
determining a set of staffing rules based on a geographic region, wherein:
- the set of rules comprises the set of staffing rules applied to the store configuration identifier and the selected staff ratio; and
- the set of workstation identifiers for the store configuration identifier corresponds to a number of workstations of each type of workstation in at least one retail store.

17. The computer-implemented method of claim 11, further comprising:
accessing the default staffing configuration deck record;
selecting specific employees for each responsibility card record of the first set of responsibility card records;

generating a first set of workstation assignments for a first operation time window; and displaying, on a plurality of workstation interface displays, the first set of workstation assignments to a user of each workstation interface display of the plurality of workstation interface displays.

18. The computer-implemented method of claim 11, further comprising:

selecting a set of staffing rules to be applied to selecting among the set of staffing configuration deck records to automatically determine the default staffing configuration deck record;

accessing the set of staffing configuration deck records and the set of staffing rules for a selected store based on the store configuration identifier; and using the set of staffing configuration deck records and the set of staffing rules for selection of workstation assignments for a plurality of operation time windows.

19. The computer-implemented method of claim 18, further comprising:

displaying, on at least one workstation display interface and for each operation time window of the plurality of operation time windows:

a time window identifier for that operation time window;

a staff ratio identifier for that operation time window; and a staffing configuration deck record for that operation time window, wherein each responsibility card record in that staffing configuration deck is populated with a staff identifier for an employee assigned to that responsibility card record.

20. A system comprising:

a pharmacy workstation comprising:

a processor;

a memory;

a network interface configured to receive a selected plurality of staffing configuration deck records corresponding to a store configuration identifier, wherein:

each staffing configuration deck record:

corresponds to an operation time window of a plurality of operation time windows and a staff ratio; and comprises a set of responsibility card records for that staffing configuration deck;

each responsibility card record comprises a workstation identifier and a staff type indicator; and the selected plurality of staffing configuration deck records are automatically determined by:

identifying a set of staff ratios corresponding to the store configuration identifier, wherein the set of staff ratios includes a plurality of staff ratios representing different combinations of employee numbers and employee types for possible staffing configurations for a set of workstation identifiers for the store configuration identifier;

automatically generating, for each staff ratio in the set of staff ratios, at least one staffing configuration deck record corresponding to that staff ratio to determine a set of staffing configuration deck records for the store configuration identifier;

evaluating, using a rules engine, a set of rules corresponding to the store configuration identifier and the plurality of staff ratios to determine each set of responsibility card records selected from the set of staffing configuration deck records; and an electronic workstation display having a graphical user interface configured to display, for each operation time window of the plurality of operation time windows:

a time window identifier for that operation time window;

a staff ratio identifier for that operation time window; and a staffing configuration deck record for that operation time window, wherein each responsibility card in that staffing configuration deck is populated with a staff identifier for an employee assigned to that responsibility card.

* * * * *